(12) United States Patent
Kellogg et al.

(10) Patent No.: US 6,582,662 B1
(45) Date of Patent: Jun. 24, 2003

(54) DEVICES AND METHODS FOR THE PERFORMANCE OF MINIATURIZED HOMOGENEOUS ASSAYS

(75) Inventors: Gregory J. Kellogg, Cambridge, MA (US); David C. Duffy, Cambridge, MA (US)

(73) Assignee: Tecan Trading AG, Mannedorf (CH)

(*) Notice: Subject to any disclaimer, the term of this patent is extended or adjusted under 35 U.S.C. 154(b) by 158 days.

(21) Appl. No.: 09/595,239

(22) Filed: Jun. 16, 2000

Related U.S. Application Data

(60) Provisional application No. 60/140,105, filed on Jun. 18, 1999.

(51) Int. Cl.[7] .................................................. G01N 9/30
(52) U.S. Cl. ..................... 422/72; 422/50; 422/68.1; 422/99; 422/100; 436/45; 436/174; 436/177; 436/180
(58) Field of Search ........................... 422/50, 61, 63, 422/64, 68.1, 72, 99–102; 436/43, 45, 174, 177, 180; 210/109, 780, 781

(56) References Cited

U.S. PATENT DOCUMENTS

| | | | |
|---|---|---|---|
| 4,683,195 A | 7/1987 | Mullis | 435/6 |
| 4,683,202 A | 7/1987 | Mullis | 435/91 |
| 4,988,617 A | 1/1991 | Landegren et al. | 435/6 |
| 5,304,487 A | 4/1994 | Wilding et al. | 435/291 |
| 5,545,540 A | 8/1996 | Mian | 435/91.2 |
| 5,876,187 A * | 3/1999 | Forster et al. | 417/322 |
| 6,063,589 A | 5/2000 | Kellogg et al. | 435/24 |
| 6,074,827 A * | 6/2000 | Nelson et al. | 435/6 |
| 6,143,247 A * | 11/2000 | Sheppard, Jr. et al. | 422/63 |
| 6,319,468 B1 * | 11/2001 | Sheppard, Jr. et al. | 422/63 |
| 6,319,469 B1 * | 11/2001 | Mian et al. | 422/64 |
| 6,338,820 B1 * | 1/2002 | Hubbard et al. | 422/64 |

FOREIGN PATENT DOCUMENTS

| | | |
|---|---|---|
| WO | WO92/22058 | 12/1992 |
| WO | WO93/22053 | 11/1993 |
| WO | WO97/21090 | 6/1997 |
| WO | WO98/07019 | 2/1998 |
| WO | WO98/28623 | 7/1998 |
| WO | WO98/53311 | 11/1998 |

OTHER PUBLICATIONS

Birnboim & Doly, 1979, Nucl. Acids Res. 7:1513–1522.
Wilding et al., 1994 Clin Chem. 40:43–47.
Kopp et al. 1998 Science 280:1046.
Larson 1997, Micro Structure Bull. 1:3.
Duffy et al. 1998, Anal. Chem 70:49744984.

* cited by examiner

Primary Examiner—Jill Warden
Assistant Examiner—Dwayne K. Handy
(74) Attorney, Agent, or Firm—McDonnell Boehnen Hulbert & Berghoff

(57) ABSTRACT

This invention relates to methods and apparatus for performing microanalytic and microsynthetic analyzes and procedures. The invention provides a microsystem platform and a micromanipulation device for manipulating the platform that utilizes the centripetal force resulting from rotation of the platform to motivate fluid movement through microchannels. These assays may be performed for a variety of purposes, including but not limited to screening of drug candidate compounds, life sciences research, and clinical and molecular diagnostics. Methods specific for the apparatus of the invention for performing any of a wide variety of microanalytical or microsynthetic processes are provided.

40 Claims, 16 Drawing Sheets

"Benchtop" trypsin inhibition assays

Trypsin inhibition assays performed on the disc of the invention

DEVICES AND METHODS FOR THE PERFORMANCE OF MINIATURIZED HOMOGENEOUS ASSAYS

This application claims priority to U.S. Provisional Application Serial No. 60/140,105, filed Jun. 18, 1999, the disclosure of which is explicitly incorporated by reference herein.

BACKGROUND OF THE INVENTION

1. Field of the Invention

This invention relates to methods and apparatus for performing microanalytic and microsynthetic analyses and procedures. In particular, the invention relates to microminiaturization of genetic, biochemical and bioanalytic processes. Specifically, the present invention provides devices and methods for the performance of miniaturized biochemical assays. These assays may be performed for a variety of purposes, including but not limited to screening of drug candidate compounds, life sciences research, and clinical and molecular diagnostics. Methods for performing any of a wide variety of such microanalytical or microsynthetic processes using the microsystems apparatus of the invention are also provided.

2. Background of the Related Art

Recent developments in a variety of investigational and research fields have created a need for improved methods and apparatus for performing analytical, particularly bioanalytical assays at microscale (i.e., in volumes of less than 100 $\mu$L). In the field of pharmaceuticals, for example, an increasing number of potential drug candidates require assessment of their biological function. As an example, the field of combinatorial chemistry combines various structural sub-units with differing chemical affinities or configurations into molecules; in theory, a new molecule having potentially unique biochemical properties can be created for each permutation of the sub-units. In this way, large libraries of compounds may be synthesized from relatively small numbers of constituents, each such compound being a potential drug lead compound of usually unknown biological activity and potency.

More traditional approaches to compound library development are also yielding growing numbers of candidates, including the use of naturally-derived compounds extracted from plants, fungi, and bacteria. In part, this is due to a growing understanding of the function of these compounds, including how they affect the metabolic pathways of the organisms which synthesize and use them; the increasing refinement in identifying and understanding compounds based on small structural and compositional differences; and improved methods for extracting and purifying these compounds.

Increased numbers of potential targets for these drug candidates are also being identified. Recent advances in biology, most notably the human genome project, have discovered many molecules whose biochemical activity is implicated in various disease states. Although these novel targets can provide exquisitely precise and specific indicia of how biological processes underlying disease can be effectively controlled and manipulated, drugs must be identified, usually by screening processes, to find compounds that can enhance, diminish, or otherwise alter these targets' ability to affect the metabolic pathways associated with disease.

The function of drug candidates, targets, and the effect of the candidates on targets is assessed in the early stages of pharmaceutical development through a process of screening that typically includes: binding of a drug candidate to a portion or domain of the target molecule; immunoassays that bind to drug candidate target domains correlated with drug efficacy; enzymatic assays, in which the inhibition of an enzymatic activity of the target by the drug candidate can be used as a sign of efficacy; protein/protein binding; and protein/DNA(RNA) binding. Additional assays involve the use of living cells and include gene expression, in which levels of transcription in response to a drug candidate are monitored, and functional assays designed to investigate both macroscopic effects, such as cell viability, as well as biochemical effects and products produced in and by the cells as a result of treatment with the drug lead compound. (Wallace & Goldman, 1997, "Bioassay Design and Implementation", in *High-Throughput Screening: The Discovery of Bioactive Substances,* J. P. Devlin, ed., Marcel Dekker, Inc.: New York, pp. 279–305).

In initial screening of compounds against targets, the number of possible screens is roughly the number of candidates multiplied by the number of targets. As a result of the growth in both the number of candidates and the number of targets, the number of assays that must be performed is growing rapidly. In addition to the increasing the number of assays to be performed, it is desirable to reduce the time required to perform the assays in order to obtain results of such screenings in a timely and useful fashion. Finally, "multiplexing" technology that allows the performance of multiple assays on one sample within a single reaction well—for example, by using readily-distinguishable signals, such as fluorescent moieties with different characteristic wavelengths—can be used to increase throughput.

In addition to drug screening assays, biological research has uncovered a vast reservoir of genetic information and diversity having little if any correlation with the function of the gene products encoded by the deciphered DNA. On the one hand, the identification of the nucleotide sequence of the human genome, coupled with bioinformatics analysis of these sequences, has identified a larger number of protein coding sequences (termed "open reading frames") that can and probably do encode functional proteins. However, since these sequences have been uncovered by simply "reading" a sequence without any information (such as the correlation of a genetic locus with a mutation associated with a disease), the function of the gene products of such a locus must be determined in order to fully understand and identify what protein target is encoded thereby and what utility drug candidates directed to such a target might have. On the other hand, human genome sequencing efforts have also identified genetic mutations (such as single nucleotide polymorphisms, or "SNPs") that may or may not be associated with human disease. In either instance, the products of this human genetic information must be assayed to determine the activity of the genes, both "wild-type" and mutant, encoded at each new genetic locus. Progress in life sciences research requires researchers to perform large numbers of assays as they investigate the structure and function of proteins coded by the growing number of identified genes in the human genome. Many of the same assays and assay formats used in drug screening may be used in other life sciences research.

Large numbers of assays must also be performed in the field of molecular diagnostics, in which individuals can now be assayed for genetic mutation associated with a disease state or the propensity to develop a disease state. For example, any particular disease or propensity for disease may be associated with several different mutations in more than one gene that can determine disease susceptibility or severity. In the monitoring of a disease state, a disease may have a "fingerprint" consisting of certain genes the expression level of which can be used diagnostically to predict the severity of the disease. Monitoring expression levels of these genes can provide an indication of the response (or lack of response) to different treatment modalities.

For these and other applications in drug discovery, life sciences research, and molecular and clinical diagnostics there exists a need for systems and assay methods that can perform very many assays in a highly-parallel fashion at low cost. The primary approach has been and will continue to be to miniaturize existing assays in order to decrease compound and reagent costs (that scale with the volume required for performing the assay). Miniaturization has been accompanied by the development of more sensitive detection schemes, including both better detectors for conventional signals (e.g., calorimetric absorption, fluorescence, and chemiluminescence) as well as new chemistries or assay formats (e.g., imaging, optical scanning, and confocal microscopy).

Miniaturization can also confer performance advantages. At short length scales, diffusionally-limited mixing is rapid and can be exploited to create sensitive assays (Brody et al., 1996, *Biophyscal J*. 71: 3430–3431). Because fluid flow in miniaturized pressure-driven systems is laminar, rather than turbulent, processes such as washing and fluid replacement are well-controlled. Microfabricated systems also enable assays that rely on a large surface area to volume ratio such as those that require binding to a surface and a variety of chromatographic approaches The development of fluid-handling and processing for miniaturized assays has primarily involved scaling down of conventional methods. The vast majority of initial drug screens have been performed in 96-well microtiter plates with operating volumes of less than 0.5 mL. The wells of these plates serve as "test tubes" for reactions as well as optical cuvettes for detection. Fluids are typically delivered to these plates using automated pipetting stations or external tubing and pumps; automation is also required for handling of plates and delivery to sub-systems such as plate washers (used in solid phase assays, for example).

Miniaturization has led to the creation of 384-well and 1536-well microtiter plates for total reaction volumes of between 0.015 and 0.1 mL. However, a number of problems arise when miniaturizing standard plate technology. First, because the total volumes are smaller and the plates are open to the environment, evaporation of fluid during the course of an assay can compromise results. Another drawback of open plates is the existence of a fluid meniscus in the well. Meniscuses of varying configurations (due, for example to imperfections in the plate or differences in contact angle and surface tension) can distort the optical signals used to interrogate the samples. As the strength of the optical signals decreases with decreasing assay volume, correction for background distortions becomes more difficult. Finally, optical scanning systems for high-density plates are often complex and expensive. Methods that minimize evaporation, provide a more uniform optical pathway, and provide simpler detection schemes are desirable.

Highly accurate pipetting technologies have been developed to deliver fluids in precisely metered quantities to these plates. Most of these fluid-delivery methods for low volumes (below a few microliters) rely on expensive piezoelectric pipetting heads that are complex and difficult to combine or "gang" into large numbers of independent pipettors so that many wells may be addressed independently. As a result, fluid delivery is either completely or partially serial (i.e., a single micropipettor, or a small number of parallel delivery systems used repeatedly to address the entire plate). Serial pipetting defeats the aim of parallelism by increasing the amount of time required to address the plate. Methods that reduce the number and precision of fluid transfer steps are therefore needed.

Fluid processing in microtiter plates is also difficult. The small dimensions of the wells, while enhancing diffusional mixing, suppress turbulence and make difficult mixing on length scales between a few tens of microns and a few millimeters. For similar reasons, washing, an important step in many assays can be problematic. Methods that reduce both the number of manipulations of fluids on the plate as well as manipulations of the plate itself (such as passing the plate to and from washing stations) can reduce cost while improving assay quality through suppression of contamination, carry-over, and fluid loss.

Thus, there is a need in the art for improved micromanipulation apparatus and methods for performing bioanalytic assays more rapidly and economically using less biological sample material. Relevant to this need in the art, some of the present inventors have developed a microsystem platform and a micromanipulation device to manipulate said platform by rotation, thereby utilizing the centripetal forces resulting from rotation of the platform to motivate fluid movement through microchannels embedded in the microplatform, as disclosed in co-owned U.S. Pat. No. 6,063,589, issued May 16, 2000, and co-owned and co-pending patent applications U.S. Ser. No. 08/761,063, filed Dec. 5, 1996; U.S. Ser. No. 08/768,990, filed Dec. 18, 1996; U.S. Ser. No. 08/910,726, filed Aug. 12, 1997; U.S. Ser. No. 08/995,056, filed Dec. 19, 1997; and U.S. Pat. No. 09/315,114, filed May 19, 1999, the disclosures of each of which are explicitly incorporated by reference herein.

SUMMARY OF THE INVENTION

This invention provides microsystems platforms as disclosed in co-owned U.S. Pat. No. 6,063,589, issued May 16, 2000, and co-owned and co-pending patent applications U.S. Ser. No. 08/761,063, filed Dec. 5, 1996; U.S. Ser. No. 08/768,990, filed Dec. 18, 1996; U.S. Ser. No. 08/910,726, filed Aug. 12, 1997; U.S. Ser. No. 08/995,056, filed Dec. 19, 1997; and U.S. Ser. No. 09/315,114,filed May 19, 1999, the disclosures of each of which are explicitly incorporated by reference herein.

The invention provides apparatus and methods for performing microscale processes on a microplatform, whereby fluid is moved on the platform in defined channels motivated by centripetal force arising from rotation of the platform. The first element of the apparatus of the invention is a microplatform that is a rotatable structure, most preferably a disk, the disk comprising fluid (sample) inlet ports, fluidic microchannels, reagent reservoirs, collection chambers, detection chambers and sample outlet ports, generically termed "microfluidic structures." The disk is rotated at speeds from about 1 to about 30,000 rpm for generating centripetal acceleration that enables fluid movement through the microfluidic structures of the platform. The disks of the invention also preferably comprise air outlet ports and air displacement channels. The air outlet ports and in particular the air displacement ports provide a means for fluids to displace air, thus ensuring uninhibited movement of fluids on the disk. Specific sites on the disk also preferably comprise elements that allow fluids to be analyzed, as well as detectors for each of these effectors.

The discs of this invention have several advantages over those that exist in the centrifugal analyzer art. Foremost is the fact that flow is laminar due to the small dimensions of the fluid channels; this allows for better control of processes such as mixing and washing. Secondly, the small dimensions conferred by microfabrication enable the use of "passive" valving, dependent upon capillary forces, over much wider range of rotational velocities and with greater reliability than in more macroscopic systems. To this are added the already described advantages of miniaturization.

The second element of the invention is a micromanipulation device that is a disk player/reader device that controls the function of the disk. This device comprises mechanisms and motors that enable the disk to be loaded and rotated. In addition, the device provides means for a user to operate the microsystems in the disk and access and analyze data, preferably using a keypad and computer display. The micromanipulation device also advantageous provides means for actuation of on-disc elements, such active valves; the application and control of heat to the disc for purposes of chemical or biological incubation; and means for adding fluids to and removing fluids from the discs. The micromanipulation devices of this invention are more particularly described in co-owned U.S. Pat. No. 6,063,589, issued May 16, 2000, and co-owned and co-pending patent applications U.S. Ser. No. 08/761,063, filed Dec. 5, 1996; U.S. Ser. No. 08/768,990, filed Dec. 18, 1996; U.S. Ser. No. 08/910,726, filed Aug. 12, 1997; U.S. Ser. No. 08/995,056, filed Dec. 19, 1997; and U.S. Ser. No. 09/315,114, filed May 19, 1999, the disclosures of each of which are explicitly incorporated by reference herein.

The invention specifically provides microsystems platforms comprising microfluidics components contained in one or a multiplicity of platform layers that are fluidly connected to permit transfer, mixing and assay performance on the sealed surface of the platform. The platforms preferably comprise reagent reservoirs containing a sufficient volume, preferably from about 1 nL to about 1 mL, of a reagent solution for a multiplicity of individual assays. The reagent reservoirs are fluidly connected by microchannels to one or more preferably a multiplicity of collection, and more preferably detection, chambers, and the microfluidics components arranged so that a specific volume of the reagent solution is delivered to each collection chamber. More preferably, said reagent reservoirs are fluidly connected to mixing structures, most preferably a mixing microchannel that is also fluidly connected to a sample reservoir, so that one or a plurality of reagents are mixed with sample and the resulting mixture delivered into the detection chamber. In preferred embodiments, the platform comprises a multiplicity of sample reservoirs and mixing structures fluidly connected with a multiplicity of detection chambers.

In the use of the platforms of the invention, fluids (including samples and reagents) are added to the platform when the platform is at rest. Thereafter, rotation of the platform on a simple motor motivates fluid movement through microchannels for various processing steps. In preferred embodiments, the platforms of the invention permit the use of a detector, most preferably an optical detector, for detecting the products of the assay, whereby the collection chambers comprise optical cuvettes, preferably at the outer edge of the platform, most preferably wherein the platform is scanned past a fixed detector through the action of the rotary motor. Because the platforms of the invention are most preferably constructed using microfabrication techniques as described more fully below, the volumes of fluids used may be made arbitrarily small as long as the detectors used have sufficient sensitivity.

The present invention solves problems in the current art through the use of a microfluidic disc in which centripetal acceleration is used to move fluids. It is an advantage of the microfluidics platforms of the present invention that the fluid-containing components are constructed to contain a small volume, thus reducing reagent costs, reaction times and the amount of biological material required to perform an assay. It is also an advantage that the fluid-containing components are sealed, thus eliminating experimental error due to differential evaporation of different fluids and the resulting changes in reagent concentration. Because the microfluidic devices of the invention are completely enclosed, both evaporation and optical distortion are reduced to negligible levels. The platforms of the invention also advantageously permit "passive" mixing and valving, i.e., mixing and valving are performed as a consequence of the structural arrangements of the components on the platforms (such as shape, length, position on the platform surface relative to the axis of rotation, and surface properties of the interior surfaces of the components, such as wettability as discussed below), and the dynamics of platform rotation (speed, acceleration, direction and change-of-direction), and permit control of assay timing and reagent delivery.

In alternative embodiments of the platforms of the invention, metering structures as disclosed in co-owned U.S. Pat. No. 6,063,589, issued May 16, 2000 and incorporated by reference herein, are used to distribute aliquots of reagent to each of a multiplicity of mixing structures, each mixing structure being fluidly connected to one of a multiplicity of sample reservoirs, thereby permitting parallel processing and mixing of the samples with a common reagent. This reduces the need for automated reagent distribution mechanisms, reduces the amount of time required for reagent dispensing (that can be performed in parallel with distribution of reagent to a multiplicity of reaction chambers), and permits delivery of small (nL-to-$\mu$L) volumes without using externally-applied electromotive means.

The assembly of a multiplicity of collection chambers on the platforms of the invention also permits simplified detectors to be used, whereby each individual collection/detection chamber can be scanned using mechanisms well-developed in the art for use with, for example, CD-ROM technology. Finally, the platforms of the invention are advantageously provided with sample and reagent entry ports for filling with samples and reagents, respectively, that can be adapted to liquid delivery means known in the art (such as micropipettors).

The platforms of the invention reduce the demands on automation in at least three ways. First, the need for precise metering of delivered fluids is relaxed through the use of on-disc metering structures, as described more fully in co-owned U.S. Pat. No. 6,063,589, issued May 16, 2000, and co-owned and co-pending patent applications U.S. Ser. No. 08/761,063, filed Dec. 5, 1996; U.S. Ser. No. 08/768, 990, filed Dec. 18, 1996; U.S. Ser. No. 08/910,726, filed Aug. 12, 1997; U.S. Ser. No. 08/995,056, filed Dec. 19, 1997; and U.S. Ser. No. 09/315,114, filed May 19, 1999, the disclosures of each of which are explicitly incorporated by reference herein. By loading imprecise volumes, slightly in excess of those needed for the assay, and allowing the rotation of the disc and use of appropriate microfluidic structures to meter the fluids, much simpler (and less expensive) fluid delivery technology may be employed than is the conventionally required for high-density microtitre plate assays.

Second, the total number of fluid "delivery" events on the microfluidic platform is reduced relative to microtiter plates.

By using microfluidic structures that sub-divide and aliquot common reagents (such as reagent solutions, buffers, and enzyme substrates) used in all assays performed on the platform, the number of manual or automated pipetting steps are reduced by at least half (depending on the complexity of the assay). A reduction in fluid transfers to the device can reduce total assay time. Examples of these structures have been disclosed in co-owned U.S. Pat. No. 6,063,589, issued May 16, 2000, and incorporated by reference herein.

Finally, the invention also provides on-platform means for mixing reagents with sample and washing the resulting reaction products, removing the need for transferring the assay collection chamber(s) to a separate "wash" station. This also reduces manipulation of the assay device as well as providing controlled and integrated fluid processing.

Certain preferred embodiments of the apparatus of the invention are described in greater detail in the following sections of this application and in the drawings.

DETAILED DESCRIPTION OF PREFERRED EMBODIMENTS

Figure 1:
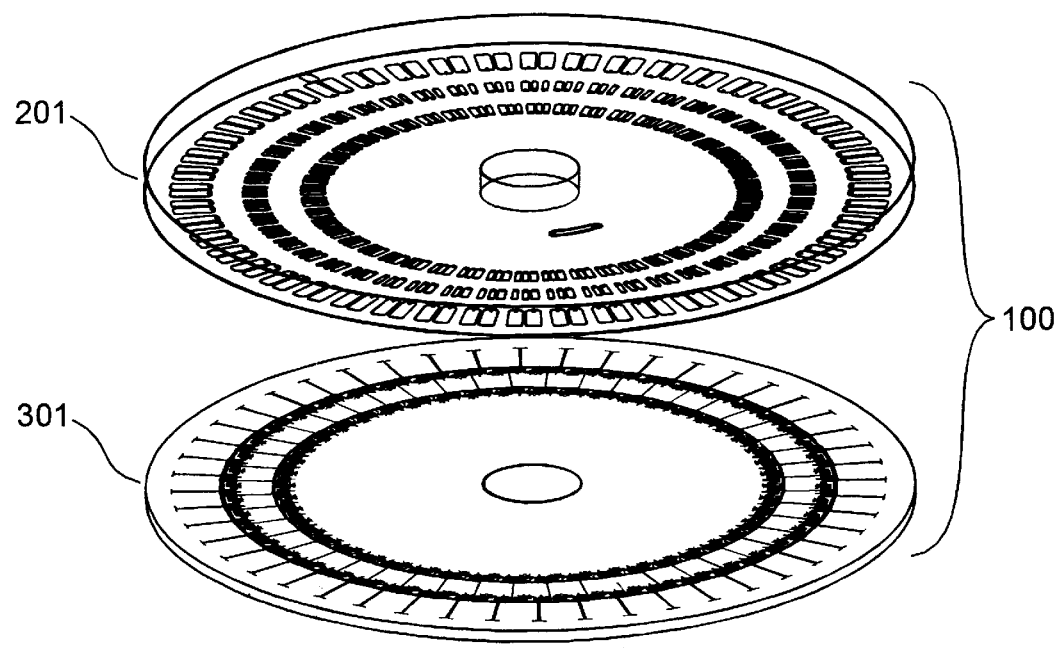
FIG. 1 depicts an exploded, oblique view of a microsystems platform of the invention.

This invention provides a microplatform and a micromanipulation device as disclosed in co-owned U.S. Pat. No. 6,063,589, issued May 16, 2000, and co-owned and co-pending patent applications U.S. Ser. No. 08/761,063, filed Dec. 5, 1996; U.S. Ser. No. 08/768,990, filed Dec. 18, 1996; U.S. Ser. No. 08/910,726, filed Aug. 12, 1997; U.S. Ser. No. 08/995,056, filed Dec. 19, 1997; U.S. Ser. No. 09/315,114, filed May 19, 1999, the disclosures of each of which are explicitly incorporated by reference herein, adapted for performing microanalytical and microsynthetic assays of biological samples.

For the purposes of this invention, the term "sample" will be understood to encompass any fluid, solution or mixture, either isolated or detected as a constituent of a more complex mixture, or synthesized from precursor species. In particular, the term "sample" will be understood to encompass any biological species of interest. The term "biological sample" or "biological fluid sample" will be understood to mean any biologically-derived sample, including but not limited to blood, plasma, serum, lymph, saliva, tears, cerebrospinal fluid, urine, sweat, plant and vegetable extracts, semen, and ascites fluid.

For the purposes of this invention, the term "a centripetally motivated fluid micromanipulation apparatus" is intended to include analytical centrifuges and rotors, microscale centrifugal separation apparatuses, and most particularly the microsystems platforms and disk handling apparatuses as described in co-owned U.S. Pat. No. 6,063,589, issued May 16, 2000, and co-owned and co-pending patent applications U.S. Ser. No. 08/761,063, filed Dec. 5, 1996; U.S. Ser. No. 08/768,990, filed Dec. 18, 1996; U.S. Ser. No. 08/910,726, filed Aug. 12, 1997; U.S. Ser. No. 08/995,056, filed Dec. 19, 1997; U.S. Ser. No. 09/315,114, filed May 19, 1999, the disclosures of each of which are explicitly incorporated by reference herein.

For the purposes of this invention, the term "microsystems platform" is intended to include centripetally-motivated microfluidics arrays as described in co-owned U.S. Pat. No. 6,063,589, issued May 16, 2000, and co-owned and co-pending patent applications U.S. Ser. No. U.S. Ser. No. 08/761,063, filed Dec. 5, 1996; U.S. Ser. No. 08/768,990, filed Dec. 18, 1996; U.S. Ser. No. 08/910,726, filed Aug. 12, 1997; U.S. Ser. No. 08/995,056, filed Dec. 19, 1997; U.S. Ser. No. 09/315,114, filed May 19, 1999, the disclosures of each of which are explicitly incorporated by reference herein.

For the purposes of this invention, the terms "capillary", "microcapillary" and "microchannel" will be understood to be interchangeable and to be constructed of either wetting or non-wetting materials where appropriate.

For the purposes of this invention, the term "reagent reservoir," "assay chamber," "fluid holding chamber," "collection chamber" and "detection chamber" will be understood to mean a defined volume on a microsystems platform of the invention comprising a fluid.

For the purposes of this invention, the terms "entry port" and "fluid input port" will be understood to mean an opening on a microsystems platform of the invention comprising a means for applying a fluid to the platform.

For the purposes of this invention, the terms "exit port" and "fluid outlet port" will be understood to mean a defined volume on a microsystems platform of the invention comprising a means for removing a fluid from the platform.

For the purposes of this invention, the term "capillary junction" will be understood to mean a region in a capillary or other flow path where surface or capillary forces are exploited to retard or promote fluid flow. A capillary junction is provided as a pocket, depression or chamber in a hydrophilic substrate that has a greater depth (vertically within the platform layer) and/ or a greater width (horizontally within the platform layer) that the fluidics component (such as a microchannel) to which it is fluidly connected. For liquids having a contact angle less than 90° (such as aqueous solutions on platforms made with most plastics, glass and silica), flow is impeded as the channel cross-section increases at the interface of the capillary junction. The force hindering flow is produced by capillary pressure, that is inversely proportional to the cross sectional dimensions of the channel and directly proportional to the surface tension of the liquid, multiplied by the cosine of the contact angle of the fluid in contact with the material comprising the channel. The factors relating to capillarity in microchannels according to this invention have been discussed in co-owned U.S. Pat. No. 6,063,589, issued May 12, 2000 and in co-owned and co-pending U.S. patent application, Ser. No. 08/910,726, filed Aug. 12, 1997, incorporated by reference in its entirety herein.

Capillary junctions can be constructed in at least three ways. In one embodiment, a capillary junction is formed at the junction of two components wherein one or both of the lateral dimensions of one component is larger than the lateral dimension(s) of the other component. As an example, in microfluidics components made from "wetting" or "wettable" materials, such a junction occurs at an enlargement of a capillary as described in co-owned and co-pending U.S. Ser. No. 08/761,063, filed Dec. 5, 1996; U.S. Ser. No. 08/768,990, filed Dec. 18, 1996; and U.S. Ser. No. 08/910,726, filed Aug. 12, 1997. Fluid flow through capillaries is inhibited at such junctions. At junctions of components made from non-wetting or non-wettable materials, on the other hand, a constriction in the fluid path, such as the exit from a chamber or reservoir into a capillary, produces a capillary junction that inhibits flow. In general, it will be understood that capillary junctions are formed when the dimensions of the components change from a small diameter (such as a capillary) to a larger diameter (such as a chamber) in wetting systems, in contrast to non-wettable systems, where capillary junctions form when the dimensions of the components change from a larger diameter (such as a chamber) to a small diameter (such as a capillary).

A second embodiment of a capillary junction is formed using a component having differential surface treatment of a capillary or flow-path. For example, a channel that is hydrophilic (that is, wettable) may be treated to have discrete regions of hydrophobicity (that is, non-wettable). A fluid flowing through such a channel will do so through the hydrophilic areas, while flow will be impeded as the fluid-vapor meniscus impinges upon the hydrophobic zone.

The third embodiment of a capillary junction according to the invention is provided for components having changes in both lateral dimension and surface properties. An example of such a junction is a microchannel opening into a hydrophobic component (microchannel or reservoir) having a larger lateral dimension. Those of ordinary skill will appreciate how capillary junctions according to the invention can be created at the juncture of components having different sizes in their lateral dimensions, different hydrophilic properties, or both.

For the purposes of this invention, the term "capillary action" will be understood to mean fluid flow in the absence of rotational motion or centripetal force applied to a fluid on a rotor or platform of the invention and is due to a partially or completely wettable surface.

For the purposes of this invention, the term "capillary microvalve" will be understood to mean a capillary microchannel comprising a capillary junction whereby fluid flow is impeded and can be motivated by the application of pressure on a fluid, typically by centripetal force created by rotation of the rotor or platform of the invention. Capillary microvalves will be understood to comprise capillary junctions that can be overcome by increasing the hydrodynamic pressure on the fluid at the junction, most preferably by increasing the rotational speed of the platform.

For the purposes of this invention, the term "in fluid communication" or "fluidly connected" is intended to define components that are operably interconnected to allow fluid flow between components. In preferred embodiments, the platform comprises a rotatable platform, more preferably a disk, whereby fluid movement on the disk is motivated by centripetal force upon rotation of the disk.

For the purposes of this invention, the term "air displacement channels" will be understood to include ports in the surface of the platform that are contiguous with the components (such as microchannels, chambers and reservoirs) on the platform, and that comprise vents and microchannels that permit displacement of air from components of the platforms and rotors by fluid movement.

The microplatforms of the invention (preferably and hereinafter collectively referred to as "disks"; for the purposes of this invention, the terms "microplatform", "microsystems platform" and "disk" are considered to be interchangeable) are provided to comprise one or a multiplicity of microsynthetic or microanalytic systems (termed "microfluidics structures" herein). Such microfluidics structures in turn comprise combinations of related components as described in further detail herein that are operably interconnected to allow fluid flow between components upon rotation of the disk. These components can be microfabricated as described below either integral to the disk or as modules attached to, placed upon, in contact with or embedded in the disk. For the purposes of this invention, the term "microfabricated" refers to processes that allow production of these structures on the sub-millimeter scale. These processes include but are not restricted to molding, photolithography, etching, stamping and other means that are familiar to those skilled in the art.

The invention also comprises a micromanipulation device for manipulating the disks of the invention, wherein the disk is rotated within the device to provide centripetal force to effect fluid flow on the disk. Accordingly, the device provides means for rotating the disk at a controlled rotational velocity, for stopping and starting disk rotation, and advantageously for changing the direction of rotation of the disk. Both electromechanical means and control means, as further described herein, are provided as components of the devices of the invention. User interface means (such as a keypad and a display) are also provided, as further described in co-owned U.S. Pat. No. 6,063,589, issued May 16, 2000, and co-owned and co-pending patent applications U.S. Ser. No. U.S. Ser. No. 08/761,063, filed Dec. 5, 1996; U.S. Ser. No. 08/768,990, filed Dec. 18, 1996; U.S. Ser. No. 08/910,726, filed Aug. 12, 1997; U.S. Ser. No. 08/995,056, filed Dec. 19, 1997; 09/315,114, filed May 19, 1999, the disclosures of each of which are explicitly incorporated by reference herein.

The invention provides a combination of specifically-adapted microplatforms that are rotatable, analytic/synthetic microvolume assay platforms, and a micromanipulation device for manipulating the platform to achieve fluid movement on the platform arising from centripetal force on the platform as result of rotation. The platform of the invention is preferably and advantageously a circular disk; however, any platform capable of being rotated to impart centripetal for a fluid on the platform is intended to fall within the scope of the invention. The micromanipulation devices of the invention are more fully described in co-owned and co-pending U.S. Ser. No. 08/761,063, filed Dec. 5, 1996; U.S. Ser. No. 08/768,990, filed Dec. 18, 1996; U.S. Ser. No. 08/910,726, filed Aug. 12, 1997; U.S. Ser. No. 08/995,056, filed Dec. 19, 1997; and U.S. Ser. No. 09/315,114, filed May 19, 1999, the disclosures of each of which are explicitly incorporated by reference herein.

Fluid (including reagents, samples and other liquid components) movement is controlled by centripetal acceleration due to rotation of the platform. The magnitude of centripetal acceleration required for fluid to flow at a rate and under a pressure appropriate for a particular microfluidics structure on the microsystems platform is determined by factors including but not limited to the effective radius of the platform, the interior diameter of microchannels, the position angle of the microchannels on the platform with respect to the direction of rotation, and the speed of rotation of the platform. In certain embodiments of the methods of the invention an unmetered amount of a fluid (either a sample or reagent solution) is applied to the platform and a metered amount is transferred from a fluid reservoir to a microchannel, as described in co-owned U.S. Pat. No. 6,063,589, issued May 16, 2000, and co-owned and copending patent applications U.S. Ser. No. 08/761,063, filed Dec. 5, 1996; U.S. Ser. No. 08/768,990, filed Dec. 18, 1996; U.S. Ser. No. 08/910,726, filed Aug. 12, 1997; U.S. Ser. No. 08/995,056, filed Dec. 19, 1997; U.S. Ser. No. 09/315,114, filed May 19, 1999, the disclosures of each of which are explicitly incorporated by reference herein. In referred embodiments, the metered amount of the fluid sample provided on an inventive platform is from about 1 nL to about 500 µL. In these embodiments, metering manifolds comprising one or a multiplicity of metering capillaries are provided to distribute the fluid to a plurality of components of the microfluidics structure.

The components of the platforms of the invention are in fluidic contract with one another. In preferred embodiments, fluidic contact is provided by microchannels comprising the surface of the platforms of the invention. Microchannel sizes are optimally determined by specific applications and by the amount of and delivery rates of fluids required for each particular embodiment of the platforms and methods of the invention. Microchannel sizes can range from 0.1 µm to a value close to the thickness of the disk (e.g., about 1 mm); in preferred embodiments, the interior dimension of the microchannel is from 0.5 µm to about 500 µm. Microchannel and reservoir shapes can be trapezoid, circular or other geometric shapes as required. Microchannels preferably are embedded in a microsystem platform having a thickness of about 0.1 to 25 mm, wherein the cross-sectional dimension of the microchannels across the thickness dimension of the platform is less than 1 mm, and can be from 1 to 90 percent of said cross-sectional dimension of the platform. Sample reservoirs, reagent reservoirs, reaction chambers, collection chambers, detections chambers and sample inlet and outlet ports preferably are embedded in a microsystem platform having a thickness of about 0.1 to 25 mm, wherein the cross-sectional dimension of the microchannels across the thickness dimension of the platform is from 1 to 75 percent of said cross-sectional dimension of the platform. In preferred embodiments, delivery of fluids through such channels is achieved by the coincident rotation of the platform for a time and at a rotational velocity sufficient to motivate fluid movement between the desired components.

The flow rate through a microchannel of the invention is inversely proportional to the length of the longitudinal extent or path of the microchannel and the viscosity of the fluid and directly proportional to the product of the square of the hydraulic diameter of the microchannel, the square of the rotational speed of the platform, the average distance of the fluid in the channels from the center of the disk and the radial extent of the fluid subject to the centripetal force. Since the hydraulic diameter of a channel is proportional to the ratio of the cross-sectional area to cross-sectional perimeter of a channel, one can judiciously vary the depth and width of a channel to affect fluid flow (see Duffy et al., 1998, *Anal. Chem.* 71: 4669–4678 and co-owned and co-pending patent applications U.S. Ser. No. 08/761,063, filed Dec. 5, 1996 and U.S. Ser. No. 08/768,990, filed Dec. 18, 1996, incorporated by reference).

For example, fluids of higher densities flow more rapidly than those of lower densities given the same geometric and rotational parameters. Similarly, fluids of lower viscosity flow more rapidly than fluids of higher viscosity given the same geometric and rotational parameters. If a microfluidics structure is displaced along the radial direction, thereby changing the average distance of the fluid from the center of the disc but maintaining all other parameters, the flow rate is affected: greater distances from the center result in greater flow rates. An increase or a decrease in the radial extent of the fluid also leads to an increase or decrease in the flow rate. These depencies are all linear. Variation in the hydraulic diameter results in a quartic dependence of flow rate on hydraulic diameter (or quadratic dependence of fluid flow velocity on hydraulic diameter), with larger flow rates corresponding to larger diameters. Finally, an increase in the rotational rate results in a quadratic increase in the flow rate or fluid flow velocity.

Input and output (entry and exit) ports are components of the microplatforms of the invention that are used for the introduction or removal of fluid components. Entry ports are provided to allow samples and reagents to be placed on or injected onto the disk; these types of ports are generally located towards the center of the disk. Exit ports are also provided to allow products to be removed from the disk. Port shape and design vary according specific applications. For example, sample input ports are designed, inter alia, to allow capillary action to efficiently draw the sample into the disk. In addition, ports can be configured to enable automated sample/reagent loading or product removal. Entry and exit ports are most advantageously provided in arrays, whereby multiple samples are applied to the disk or to effect product removal from the microplatform.

In some embodiments of the platforms of the invention, the inlet and outlet ports are adapted to the use of manual pipettors and other means of delivering fluids to the reservoirs of the platform. In alternative, advantageous embodiments, the platform is adapted to the use of automated fluid loading devices. One example of such an automated device is a single pipette head located on a robotic arm that moves in a direction radially along the surface of the platform. In this embodiment, the platform could be indexed upon the spindle of the rotary motor in the azimuthal direction beneath the pipette head, which would travel in the radial direction to address the appropriate reservoir.

Another embodiment is a pipettor head adapted to address multiple reservoirs, either a subset of or all of the reservoirs on the platform surface. For embodiments where the pipettor head addresses a subset of the reservoirs, a single head can involve three pipetting units: one for each of the fluids used in a given assay, arranged in a configuration such that all three reservoirs may be addressed without changing the spatial relationship of the pipettes to one another. This could be enlarged to a head with six such pipettors, three for the inner ring and three for the outer ring, as illustrated in FIG. 1. Larger numbers of heads could be used but "sparsely" distributed around the platform (for example, 24 heads over 360 degrees). Indexing of an arm containing the head or the table beneath the head could be used to effect filling of the entire disc. Finally, specially-designed heads that address all reservoirs are also advantageously provided.

Also included in air handling systems on the disk are air displacement channels, whereby the movement of fluids displaces air through channels that connect to the fluid-containing microchannels retrograde to the direction of movement of the fluid, thereby providing a positive pressure to further motivate movement of the fluid.

Platforms of the invention such as disks and the microfluidics components comprising such platforms are advantageously provided having a variety of composition and surface coatings appropriate for particular applications. Platform composition will be a function of structural requirements, manufacturing processes, and reagent compatibility/chemical resistance properties. Specifically, platforms are provided that are made from inorganic crystalline or amorphous materials, e.g. silicon, silica, quartz, inert metals, or from organic materials such as plastics, for example, poly(methyl methacrylate) (PMMA), acetonitrile-butadiene-styrene (ABS), polycarbonate, polyethylene, polystyrene, polyolefins, polypropylene and metallocene. These may be used with unmodified or modified surfaces as described below. The platforms may also be made from thermoset materials such as polyurethane and poly(dimethyl siloxane) (PDMS). Also provided by the invention are platforms made of composites or combinations of these materials; for example, platforms manufactures of a plastic material having embedded therein an optically transparent glass surface comprising the detection chamber of the platform. Alternately, platforms composed of layers made from different materials may be made. The surface properties of these materials may be modified for specific applications, as disclosed in co-owned U.S. Pat. No. 6,063,589, issued May 16, 2000, and co-owned and co-pending patent applications U.S. Ser. No. 08/761,063, filed Dec. 5, 1996; U.S. Ser. No. 08/768,990, filed Dec. 18, 1996; U.S. Ser. No. 08/910,726, filed Aug. 12, 1997; U.S. Ser. No. 08/995,056, filed Dec. 19, 1997; and U.S. Ser. No. 09/315,114, filed May 19, 1999, the disclosures of each of which are explicitly incorporated by reference herein.

Preferably, the disk incorporates microfabricated mechanical, optical, and fluidic control components on platforms made from, for example, plastic, silica, quartz, metal or ceramic. These structures are constructed on a sub-millimeter scale by molding, photolithography, etching, stamping or other appropriate means, as described in more detail below. It will also be recognized that platforms comprising a multiplicity of the microfluidic structures are also encompassed by the invention, wherein individual combinations of microfluidics and reservoirs, or such reservoirs shared in common, are provided fluidly connected thereto. An example of such a platform is shown in FIG. 1.

Platform Manufacture and Assembly

Microfluidics structures are provided embedded in a substrate comprising the microsystems platform of the invention. The platform is preferably manufactured and assembled as layers containing separate components that are bonded together. As illustrated in FIG. 1, the exemplified embodiment of the platforms of the invention comprise two layers, a reservoir layer and a microfluidics layer. Platforms having additional layers are also within the scope of the invention.

The reservoir layer of the platform is manufactured from a thermoplastic material such as acrylic, polystyrene, polycarbonate, or polyethylene. For such materials, fabrication methods include machining and conventional injection molding. For injection molding, the mold inserts that are used to define the features of the platform can be created using standard methods of machining, electrical discharge machining, and other means known in the art.

The reservoir layer of the platform can also be manufactured from a thermoset material or other material that exists in a liquid form until subjected to heat, radiation, or other energy sources. Examples of thermoset materials include poly(dimethyl siloxane) (PDMS), polyurethane, or epoxy. Typically, these materials are obtained from the manufacturer in two parts; the two parts are mixed together in a prescribed ratio, injected into or poured over a mold and subjected to heat to initiate and complete cross-linking of the monomers present in the pre-polymer fluid. The process of rapidly injecting a pre-polymer fluid into a mold and then cross-linking or curing the part is often referred to as reaction injection molding (RIM). The process of pouring a pre-polymer fluid over a mold and then allowing the part to cross-link or cure is often referred to as casting. Mold inserts for RIM or casting can be fabricated using standard methods of machining, electrical discharge machining, and other means known in the art.

The microfluidics layer of the platform can also be manufactured from a thermoplastic material such as acrylic, polystyrene, polycarbonate, or polyethylene. Because the dimensions of the channels and cuvettes may be much smaller than those found in the reservoir layer, typical fabrication methods with these materials may include not only machining and conventional injection molding but also compression/injection molding, and embossing or coining. For injection molding, the mold inserts that are used to define the features of this layer of the platform can be created using conventional methods such as machining or electrical discharge machining. For mold inserts with features too fine to be created in conventional ways, various microfabrication techniques are used. These include silicon micromachining, in which patterns are created on a silicon wafer substrate through the use of a photoresist and a photomask (Madou, 1997, *Fundamentals of Microfabricaton*, CRC Press: Boca Raton, Fla.). When the silicon wafer is subjected to an etching agent, the photoresist prevents penetration of the agent into the silicon beneath the photoresist, while allowing etching to occur in the exposed areas of the silicon. In this way patterns are etched into the silicon and can be used to create microfabricated plastic parts directly through embossing. In this process, the etched silicon is brought into contact with a flat thermoplastic sheet under high pressure and at a temperature near the glass transition temperature of the plastic. As a result, the pattern is transferred in negative into the plastic.

Etched silicon may also be used to create a metal mold insert through electroplating using, for example, metallic nickel. Silicon etched using any one of a variety of techniques such as anisotropoic or isotropic wet etching or deep reactive ion etching (DRIE) may serve as a basis for a metal mold. A seed layer of nickel is deposited through evaporation on the silicon; once such an electrically-conductie seed layer is formed, conventional electroplating techniques may be used to build a thick nickel layer. Typically, the silicon is then removed (Larsson, 1997, *Micro Structure Bull.* 1: 3). The insert is then used in conventional injection molding or compression/injection molding.

In addition to silicon micromachining for mold inserts, molds can alternatively be created using photolithography without etching the silicon. Photoresist patterns are created on silicon or other appropriate substrates. Rather than etching the silicon wafer as in silicon micromachining, the photoresist pattern and silicon are metallized through electroplating, thermal vapor deposition, or other means known in the art. The metal relief pattern then serves as a mold for coining, injection molding, or compression/injection molding as described above.

The microfluidic layer of the platform can also be manufactured using a thermoset material as described above for production of the reservoir layer, wherein the mold pattern for thermosets of the microfluidics layer is prepared as described above. Because reaction-injection molding and casting do not require the high pressures and temperatures of injection molding, a wider variety of mold patterns may be used. In addition to the use of a silicon or metal mold insert, the photoresist pattern as described can also be used as a mold relief itself. While the photoresist would not withstand the high pressures and temperatures of injection molding, the milder conditions of casting or RIM create no significant damage.

The assembly of the platform involves registration and attachment of the microfluidic layer to the reservoir layer. In order for the microfluidics structures on the platform to be useful for performing assays as described herein, certain microfluidics pathways in the reservoir layer must be connected to certain microfluidics pathways in the microfluidics layer. Registration of these microfluidics pathways may be accomplished through optical alignment of fiducial marks on the microfluidic and reservoir layers or through mechanical alignment of holes or depressions on the microfluidic layer with pins or raised features on the reservoir layer. The required registration tolerances may be relaxed by designing the microfluidics pathway in the reservoir layer to be much larger than the microfluidics pathway in the microfluidics layer, or vice versa.

Attachment may be accomplished in a number of ways, including conformal sealing, heat sealing or fusion bonding, bonding with a double-sided adhesive tape or heat-sealable film, bonding with a ultraviolet (UV) curable adhesive or a heat-curable glue, chemical bonding or bonding with a solvent.

A requirement for conformal sealing is that one or both of the layers are made of an elastomeric material and that the surfaces to be bonded are free of dust or debris that could limit the physical contact of the two layers. In a preferred assembly approach, an elastomeric microfluidics layer is registered with respect to and then pressed onto a rigid reservoir layer. The elastomeric microfluidics layer may be advantageously made of silicone and the rigid reservoir layer may be advantageously made of acrylic or polycarbonate. Hand pressure allows the layers to adhere through van der Waals forces.

A requirement for heat sealing or fusion bonding is that both the reservoir and microfluidics layers are made of thermoplastic materials and that the sealing occurs at temperatures above the glass transition temperatures, in the case of amorphous polymers, or melting temperatures, in the case of semi-crystalline polymers, of both of the layer materials. In a preferred assembly approach, the microfluidics layer is registered with respect to and pressed onto the reservoir layer, this composite disk is then placed between two flat heated blocks and pressure is applied to the composite through the heated blocks. By adjusting the temperature versus time profile at each of the faces of the composite disk and by adjusting the pressure versus time profile that is applied to the composite system, one can determine the time-temperature-pressure profile that allows for bonding of the two layers yet minimizes variation of the features within each of the layers. For example, heating two acrylic disks from room temperature to a temperature just above the glass transition temperature of acrylic at a constant pressure of 250 psi over one hour is a recipe that allows for minimal variation of 250 $\mu$m wide fluidic channels. In another assembly approach, the bond surfaces of the microfluidics and reservoir layers are separately heated in a non-contact fashion with radiative lamp and when the bond surfaces have reached their glass transition temperatures the microfluidics layer is registered with respect to and pressed onto the reservoir layer.

A double-sided adhesive tape or heat scalable film may be used to bond the microfluidics and reservoir layers. Before bonding, holes are first cut into the tape (or film) to allow for fluid communication between the two layers, the tape (or film) is registered with respect to and applied onto the reservoir layer, and the microfluidics layer is registered with respect to and applied onto the tape(or film)/reservoir layer composite. In order to bond a heat-sealable film to a surface, it is necessary to raise the temperature of the film to above the glass transition temperature, in the case of an amorphous polymer, or the melting temperature, in the case of a semicrystalline polymer, of the film's adherent polymer material. For bonding with an adhesive tape or a heat-sealable film, an adequate bond can typically be achieved with hand pressure.

A photopolymerizable polymer (for example, a UV-curable glue) or a heat-curable polymer may be used to adhere the microfluidics and reservoir layers. In one approach, this glue is applied to one or both of the layers. Application methods include painting, spraying, dip, coating or spin coating. After the application of the glue the layers are assembled and exposed to ultraviolet radiation or heat to allow for the initiation and completion of cross-linking or setting of the glue. In another approach, the microfluidics and reservoir layers are each fabricated with a set of fluid channels that are to be used only for the glue. These channels may, for example, encircle the fluid channels and cuvettes used for the assay. The microfluidics layer is registered with respect to and pressed onto the reservoir layer. The glue is pipetted into the various designated channels and after the glue has filled these channels, the assembled system is exposed to ultraviolet radiation or heat to allow for the cross-linking or setting of the glue.

When polydimethylsiloxane (PDMS) or silicone is first exposed to an oxygen plasma and then pressed onto a similarly treated silicone surface in an ambient environment, the two surfaces adhere. It is thought that the plasma treatment converts the silicone surface to a silanol surface and that the silanol groups are converted to siloxane bonds when the surfaces are brought together (Duffy et al., 1998, Anal. Chem. 70: 4974–4984). This chemical bonding approach is used to adhere the silicone microfluidics and reservoir layer.

A requirement for solvent bonding is that the bond surfaces of both the microfluidics and reservoir layers can be solvated or plasticized with a volatile solvent. For solvent bonding, the bond surfaces are each painted with the appropriate solvating fluid or each exposed to the appropriate solvating vapor and then registered and pressed together. Plasticization allows the polymer molecules to become more mobile and when the surfaces are brought in contact the polymer molecules become entangled; once the solvent has evaporated the polymer molecules are no longer mobile and the molecules remain entangled, thereby allowing for a physical bond between the two surfaces. In another approach, the microfluidics and reservoir layers are each fabricated with a set of fluid channels that are to be used only for the solvent and the layers are bonding much like they are with the UV-curable or heat-curable glue as described above.

Referring now to the Figures for a more thorough description of the invention, FIG. 1 shows an exploded view of an example of a disc appropriate for large numbers of similar or identical microfluidics structures for performing, inter alia, liquid-phase assays. The disc shown here performs 96 assays of the general form: mix first fluid A with second fluid B, and then mix the combined fluids (A+B) with third fluid C. These assays are "independent": fluids A, B, and C are loaded through appropriate entry ports into the individual reservoirs for each assay. In this way, fluids A, B, and C need not be identical for all assays, but can be chosen by the user. As described more fully below, platforms having a greater number of such microfluidics structures are contemplated by the invention.

This disc illustrates that identical assays may be made by repeating microfluidics structures around the disc at a given radius as well as modifying the structures for placement at different radial positions. In this way, it is possible to fully cover the surface of the disc with microfluidics structures for performing assays. The maximum number of assays that may be performed will depend upon the volume of fluid that may be manipulated reproducibly, i.e., the minimum reproducible dimensions with which the disc may be fabricated, and the amount of hydrodynamic pressure required to drive small volumes of fluid through microchannels at convenient rotational rates. Taking these considerations into account, it is estimated that greater than 10,000 assays having volumes of 1–5 nL can be created in a circular platform having a 6 cm radius.

In FIG. 1, platform 100 is composed of at least two component layers. A reservoir layer 201 is bonded to a microfluidics layer 301. The bottom face of the reservoir layer, when mated with the microfluidic layer described below, forms a complete network of enclosed channels and reservoirs through which fluids flow under the impetus of centripetal force created by rotation of the platform about a central axis. Fluid flow permits mixing of various component fluids in the assay and movement of the fluids from sample and reagent reservoirs through mixing structures and into assay collection chambers. In addition, fluid flow can be effectuated to include incubation and wash steps, using structures disclosed in co-owned U.S. Pat. No. 6,063,589, issued May 16, 2000 and incorporated by reference herein. Fluid flow rates of from about 1 nL/s to about 1000 $\mu$L/s are achieved at rotational speeds of from about 4 to about 30,000 rpm. "Passive" or capillary valves are preferably used to control fluid flow in the platform as described in co-owned U.S. Pat. No. 6,063,589, issued May 16, 2000, and co-owned and co-pending patent applications U.S. Ser. No. 08/761,063, filed Dec. 5, 1996; U.S. Ser. No. 08/768,990, filed Dec. 18, 1996; U.S. Ser. No. 08/910,726, filed Aug. 12, 1997; U.S. Ser. No. 08/995,056, filed Dec. 19, 1997; U.S. Ser. No. 09/315,114, filed May 19, 1999, the disclosures of each of which are explicitly incorporated by reference herein. In the operation of the platforms of the invention, competition between rotationally-induced hydrostatic pressure and the capillary pressure exerted in small channels and orifices are exploited to provide a rotation-depending gating or valving system. After fluids are deposited in detection chambers positioned towards the outer edge of the platform, a signal, most preferably an optical signal, is detected.

Platform 100 is preferably provided in the shape of a disc, a circular planar platform having a diameter of from about 10 mm to about 50 mm and a thickness of from about 0.1 mm to about 25 mm. Each layer comprising the platform preferably has a diameter that is substantially the same as the other layers, although in some embodiments the diameters of the different layers are not required to completely match. Each layer has a thickness ranging from about 0.1 mm to about 25 mm, said thickness depending in part on the volumetric capacity of the microfluidics components contained therein.

Reservoir Layer

Figure 2:
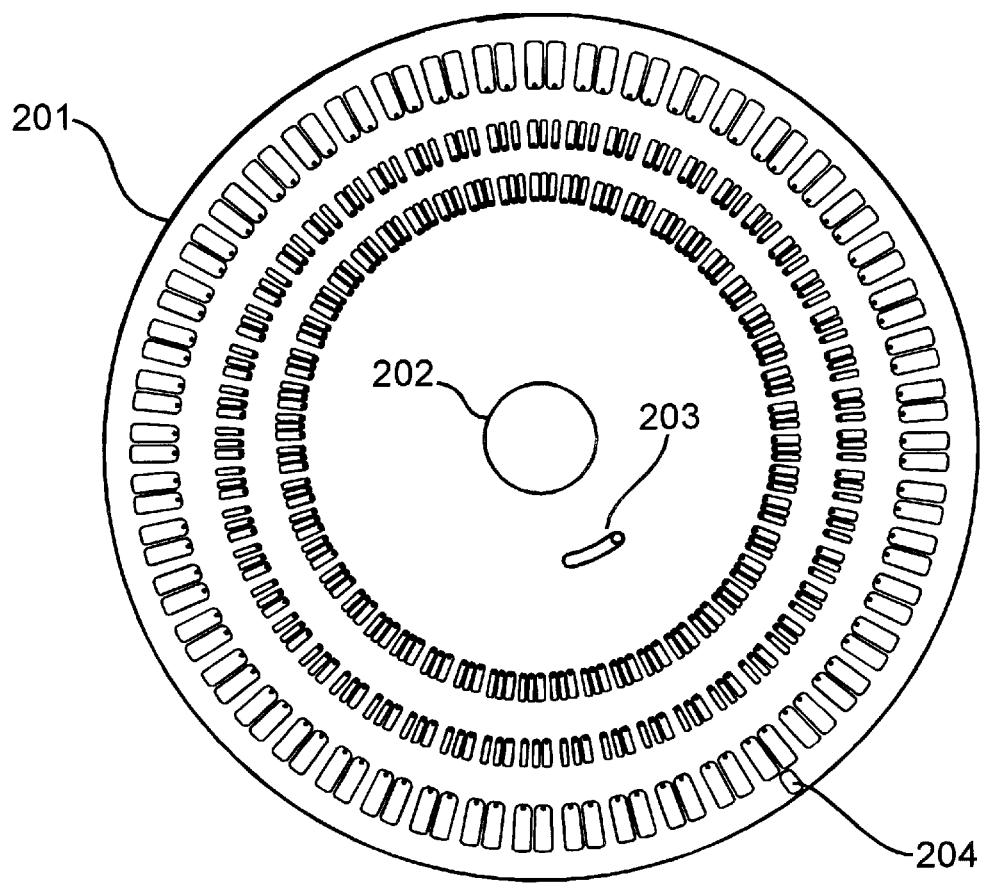
FIG. 2 depicts a plan view of one component of the microsystems platform shown in exploded, oblique view in FIG. 1, the reservoir layer.
Figure 4:
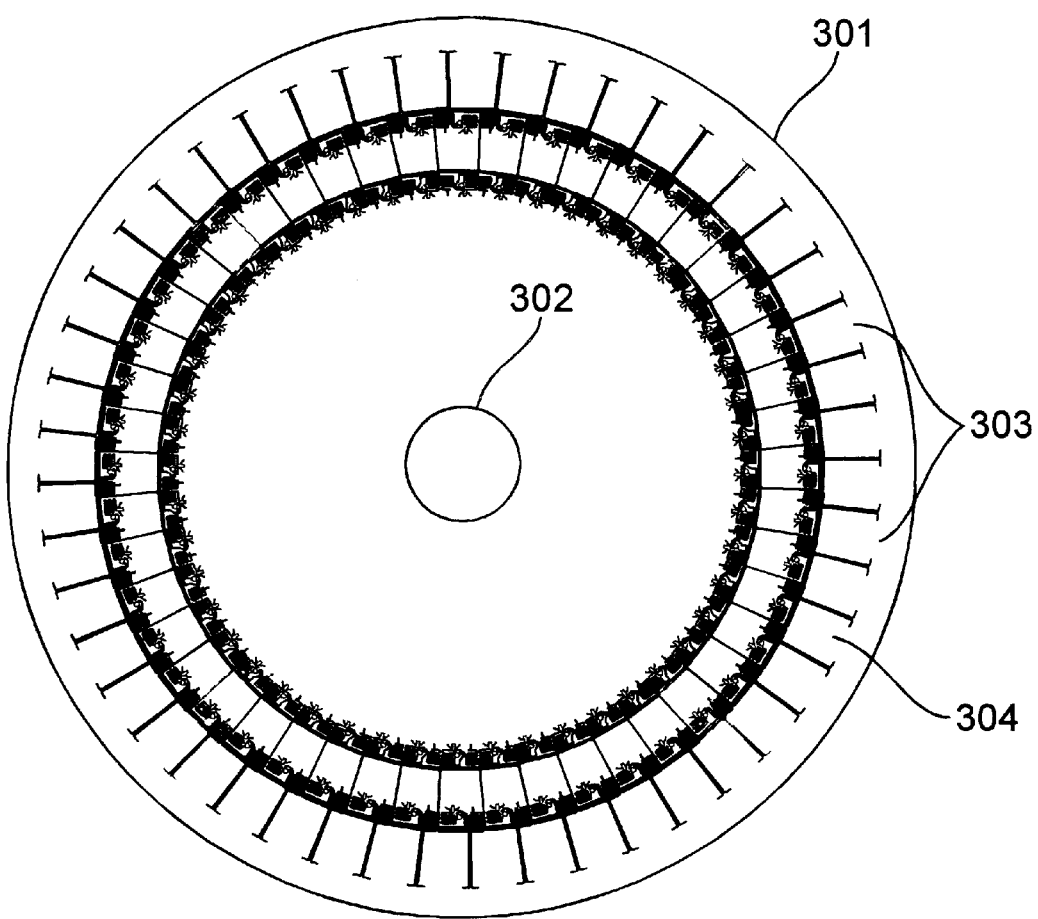
FIG. 4 shows a plan view of another component of the microsystems platform of FIG. 1, the microfluidic layer.
Figure 5:
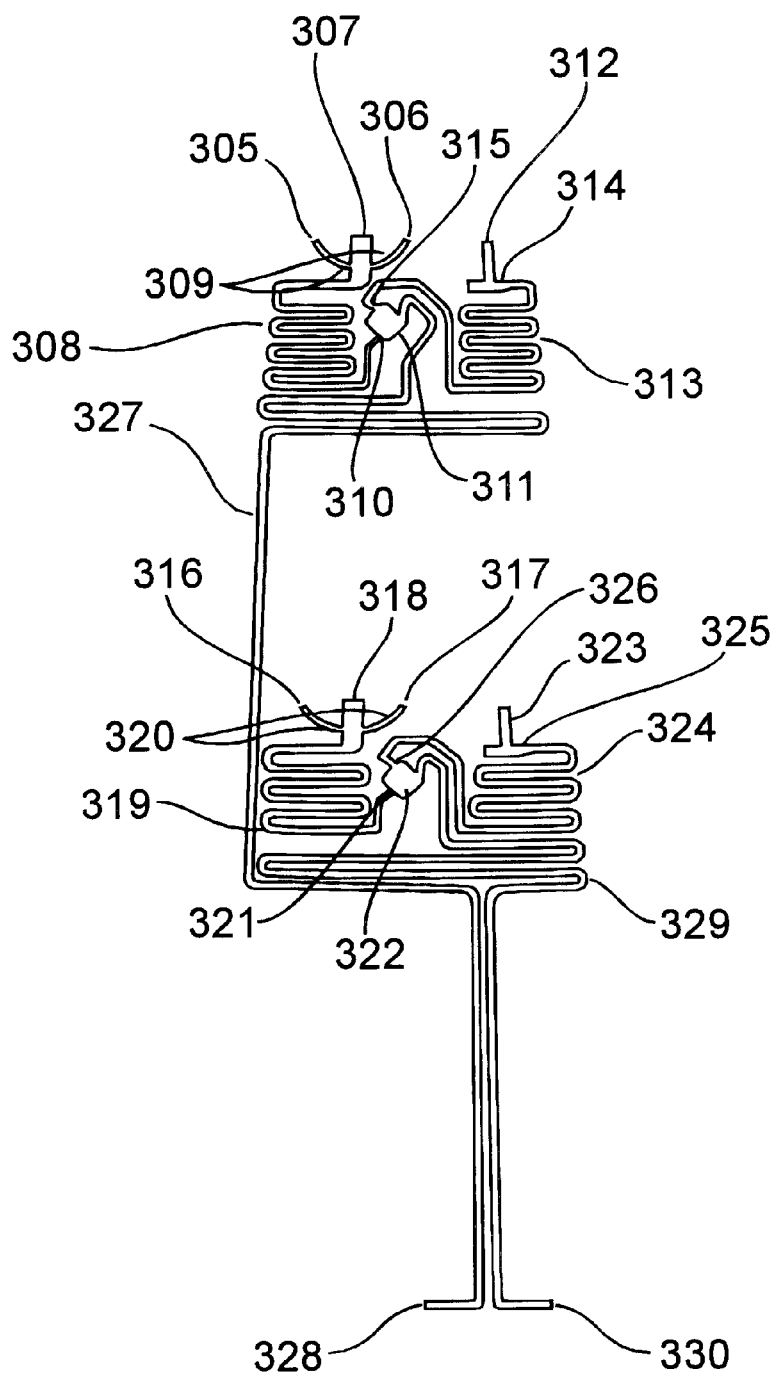
FIG. 5 is a detail of one segment of the microfluidic layer of FIG. 4 comprising the microfluidic channels for two microfluidic assay structures.

The structure of reservoir layer 201 is shown in FIG. 2, which depicts the "bottom" face to more clearly illustrate this embodiment of the platforms of the invention. By illustrating the surface in this way it is easier to see how the features are aligned with the microfluidic layer 301 (as shown in FIGS. 4 and 5 as described more fully below).

Reservoir layer 201 is preferably provided in the shape of a disc, a circular planar platform having a diameter of from about 10 mm to about 50 mm and a thickness of from about 0.1 mm to about 25 mm. The layer preferably comprises a center hole 202 for mounting on a spindle, having a diameter of from about 1 mm to about 20 mm. Center hole 202 can be replaced by an extruded fitting for connection to a spindle, or may be absent entirely, in which case registry and connection to the spindle is accomplished using the attached microfluidic layer or another portion of the surface of the platform. Reservoir layer 201 can also include registry features such as the groove 203 that permits a clamping fixture above the platform to be brought in proximity with, but not in contact with, the top surface of the platform when the platform is loaded into the spindle. In embodiments having this feature, a pin on the clamping fixture, preferably spring-loaded, slips into the groove as the disc is spun at low rpm, and captures the clamping fixture, thus determining the platform's orientation with respect thereto. In other embodiments, the platform comprises "home-flag" 204, that is a reflective or absorbing stripe that can be positioned on the surface of the platform and sensed by an emitter/photodiode pair as the disc is spun, thus permitting the orientation of the disc with respect to the instrument to be determined.

Figure 3:
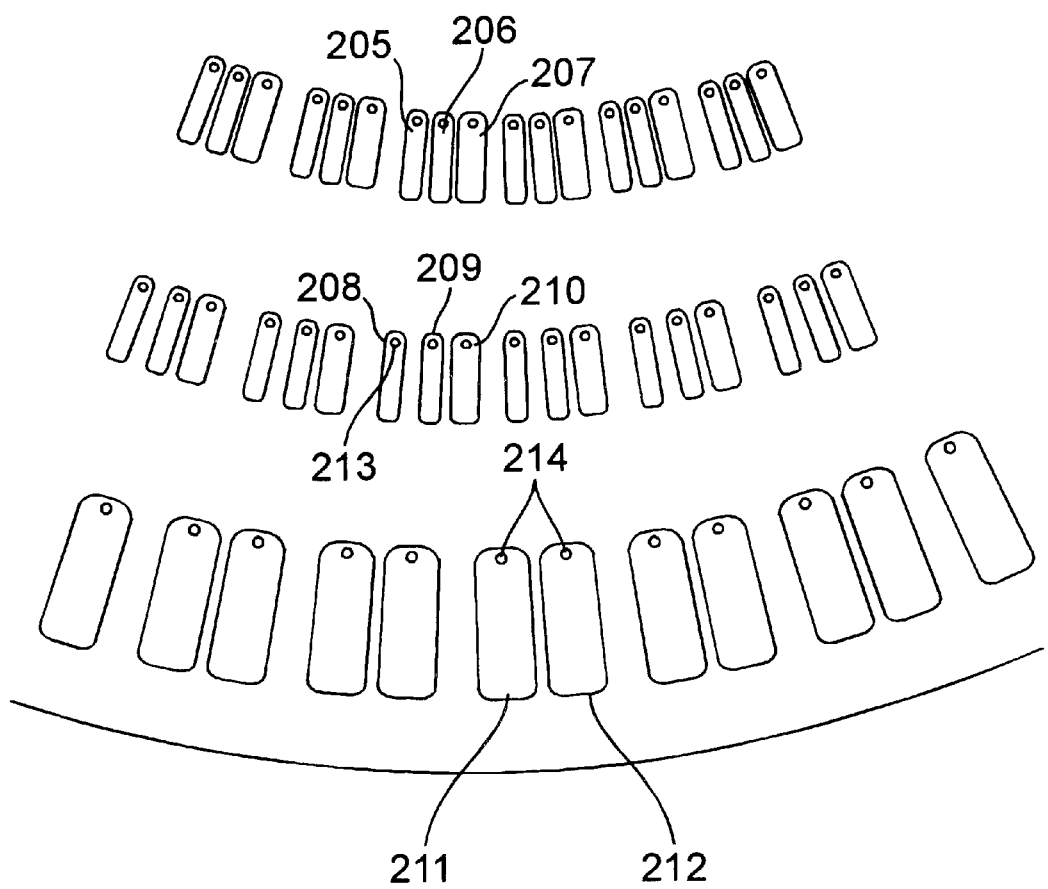
FIG. 3 is a detail of a section of the reservoir layer illustrated in FIG. 2.

FIG. 3 illustrates an expanded view of a section of the reservoir layer. As shown in the Figure, this embodiment of the platforms of the invention contains three reservoirs plus one collection/detection chamber for each assay, arrayed in two concentric rings of assays. Each reservoir has dimensions of from about 0.05 mm to about 5 mm wide, from about 0.05 mm to about 20 mm long, and from about 0.05 mm to about 5 mm thick, and has a volumetric capacity of from about 0.1 nL to about 500 $\mu$L. Reservoirs 205, 206, and 207 are designed to contain fluids A, B, and C for the inner ring of assays, while reservoir 211 is the detection chamber for the inner set of assays. Similarly, reservoirs 208, 209, and 210 contain fluids A, B, and C for the outer ring of assays, with 212 the corresponding detection chamber. This collection of eight reservoirs—205 through 212—is repeated on the illustrated platform of the invention a total of 48 times azimuthally around the disc with an angular spacing of 7.5°. Platforms having a smaller or greater number of arrays of such reservoirs are within the scope of the invention being most preferably evenly spaced around the surface area of the platform in configurations that match pattern of microfluidics components on the microfluidics layer.

The reservoirs of the inner rings also contain loading holes, 213, through which the fluids are loaded prior to use. Loading holes 213 preferably have dimensions adapted to automated loading devices such as micropipettors, for example, a standard 200 $\mu$L plastic pipette tip having a tip diameter of 1.5 mm; micropipette tips of diameter 1 mm; piezoelectric or ceramic drop delivery systems (such as are sold by the IVEK Corp., Springfield, Vt.); and inkjet-based fluid delivery systems. For non-contact delivery systems such as piezoelectric or inkjet delivery, the dimensions of the ports must be a few times greater than the size of the droplets, e.g., 0.2 mm for a 1 nL drop.

The assay collection/detection chambers also contain air displacement holes 214 that allow air displaced by the motion of fluids to escape, having a cross-sectional dimension of from about 100 to about 500 $\mu$m. These holes may optionally be replaced by a manifold or series of channels connecting the receiving reservoirs to one or more air hole.

The collection/detection chambers are designed to be accessible to optical interrogation, for example, by being composed of optically-transparent plastics or other materials.

Microfluidics Layer

The microfluidics layer of the embodiment of the platform of the invention is shown in FIGS. 4 and 5.

Microfluidics layer 301 is optimally of the same lateral dimensions as the microfluidics layer. There is also an optional center hole 302 for mounting on a spindle, although this is not required in all configurations.

The microfluidics layer contains an array 303 of microfluidic structures 304, the number of structures in the array being equal to one half of the number of parallel assays to be run on the platform. In the embodiment illustrated in the Figures, there are 48 such structures repeated with angular spacing of 7.5°. Microfluidics structures 304 preferably comprise microchannels having cross-sectional dimensions of from about 5 $\mu$m to about 500 $\mu$m and a depth in the microfluidics layer of from about 10 $\mu$m to about 3 mm.

FIG. 5 is an expanded view of a single unit of microfluidic structures. Each microfluidics structure comprises the microfluidics for one inner and one outer ring assay. The microfluidic structure consists of depressions in the surface of the microfluidic disc of a single or multiple depths ranging between 2 microns and 1000 microns, while the widths of the depressions varies from about 2 $\mu$m to about 500 $\mu$m, as further described below.

The structure of the microfluidics components of the inner assay ring is as follows. Microchannels 305 and 306 are aligned by assembly between the reservoir layer and microfluidics layer so that the microchannels protrude into reservoirs 205 and 206, respectively. The microchannel 307 is an expansion space for air displaced by fluids flowing through microchannels 305 and 306 into the microchannel 308. Microchannels 305 and 306 in some embodiments narrow to form capillary junctions 309 before joining mixing microchannel 308. Mixing microchannels are configured to provide mixing of different solutions as the mixture traverses the longitudinal extent of the microchannel. The degree of mixing is dependent on the flow rate of the fluids and the longitudinal extent of the mixing microchannel, which is proportional to the amount of time the two fluids are in contact and are mixed together. The degree of mixing is also dependent on the lateral extent of the mixing microchannel, and is further dependent on the diffusion constants of the fluids to be mixed. In order to accommodate mixing microchannels having sufficient lengths for mixing fluids having a useful range of viscosities, the mixing microchannels are provided as shown in FIG. 5. Mixing is promoted as illustrated in FIG. 5 by configuring the microchannel to bend several times as it traverses a path on the platform surface that is perpendicular to the direction of rotation, but extends radially on the surface of the platform from a position more proximal to a position more distal to the axis of rotation. Mixing microchannel 308 has a length of from about 1 mm to about 100 mm, its length in some cases achieved through the use of bends. Mixing microchannel 308 is provided with a capillary junction at 310 wherein the interior diameter of the microchannel changes by between about 0 to 95%, and then joins capillary junction 311. Capillary junction 311 is larger in the lateral or vertical direction or both than the capillary junction at 310.

Mixing in the device is promoted through diffusion. If two small volumes A and B are added to a single container, diffusion of A into B and/or B into A will effect mixing. The amount of time required for this mixing will depend upon the diffusion constants of the molecules within the solutions whose mixing is desired and the distances over which the molecules must diffuse. For example, 0.5 microliter of solution A comprising a molecule with diffusion constant D is added to a reservoir 1 mm on a side. Solution B comprising a molecule whose diffusion constant is also D is added. The solutions will initially occupy the volume with an interface partitioning them. Even if the fluids are highly miscible, the diffusion times to create a completely homogeneous solution will be approximately $t=2x^2/D$. For $x=0.05$ cm (0.5 mm) and $D=10^{-5}$ cm$^2$/s, the mixing time is 500 seconds, an unacceptably long time for most reactions. This mixing time may be reduced by mechanical stirring, for example, but stirring is difficult to obtain in fluids confined in small structures because the flow of the fluid is laminar and does not contain turbulent eddies that are known to promote mixing. If, instead of placing fluids A and then B in a 1 mm$^3$ container, fluids A and B were placed side-by-side in a long, thin capillary of lateral dimension d, the relevant time for mixing is much shorter. If, for example, d is 100 microns, mixing time t is 20 seconds. The mixing channels of the device simulate the placement of fluid in a long capillary by co-injecting fluid streams A and B into a capillary microchannel. These fluids flow side-by-side down the channel initially. As the fluid is pushed through the microchannel due to centrifugal force produced by rotation of the platform, diffusion occurs between the fluids. By choosing a capillary of sufficiently narrow diameter, sufficient length, and a pumping rate that is sufficiently low, the portion of A and B of the total volumes of A and B present in the channel during pumping can be caused to mix.

These choices may be determined by setting the required time for mixing equal to the amount of time necessary for the fluid to traverse the channel. The required time for diffusion is $$t_m \approx \frac{2w^2}{D}$$

where w is the lateral size of the channel. The amount of time necessary to traverse the channel is simply the length of the channel divided by the fluid velocity, the velocity being calculated as described in co-owned and co-pending U.S. Ser. No. 08/910,726, filed Aug. 12, 1997, and Duffy et al. (1999, *Anal. Chem.* 71: 4669–4678):

$$t_t = \frac{l}{U} = \frac{l}{\left(\frac{\rho\omega^2 \Delta R \langle R \rangle (d^H)^2}{32\eta l}\right)} = \frac{32\eta l^2}{\rho\omega^2 \Delta R \langle R \rangle (d^H)^2}$$

where the fluid properties are the density $\rho$ and viscosity $\eta$, $\Delta R$ and $\langle R \rangle$ are the extent along the radius and average radial position of the fluid subject to centripetal acceleration, and l and $d^H$ are the length and hydraulic diameter of the channel. By choosing variables such that $t_t$ is at least equal to or greater than $t_m$, mixing in the microchannels is assured.

Entry 312 to microchannel 313 protrudes into reservoir 207 and preferably forms capillary junction 314, having dimensions substantially the same as capillary junction 311. Microchannel 313 passes through a change in the lateral dimension at 315 wherein the interior diameter of the microchannel changes by between 0% and 95% and then joins capillary junction 311. The capillary junction leads to a further mixing microchannel 327 that terminates at end 328 and that protrudes into detection chamber 211. Mixing microchannel 327 has a length of from about 1 mm to about 100 mm, and preferably comprises one or a multiplicity of bends as illustrated in the Figures.

The structure of the outer ring microfluidics is as follows. Microchannels 316 and 317 are aligned by assembly between the reservoir layer and microfluidics layer so that the microchannels protrude into reservoirs 208 and 209, respectively. The microchannel 318 is an expansion space for air displaced by fluids flowing through microchannels 316 and 317 into microchannel 319. Microchannels 316 and 317 in some embodiments narrow to form capillary junctions 320 before joining mixing microchannel 319. Mixing microchannel 319 passes through a change in the lateral dimension at 321 to the capillary junction 322. Similarly, the entry 323 to microchannel 324 protrudes into reservoir 210 and may form a capillary junction 325. Microchannel 324 passes through a change in the lateral dimension at 326 to the capillary junction 322. The capillary junction leads to a further mixing microchannel 329 that terminates at end 330 that protrudes into detection chamber 212. Mixing microchannel 329 has a length of from about 1 mm to about 100 mm, and preferably comprises one or a multiplicity of bends as illustrated in the Figures.

The dimensions of the microfluidic components for the outer ring structures can (as here) be the same as for the corresponding components described above for the inner ring microfluidics structures. The dimensions of the components are chosen so that the fluid flow rates are substantially the same in each microfluidics structure, without regard to the position of the structure on the platform. The important considerations for designing the platforms of the invention are microchannel diameters, lengths, and positioning on the disc, which determines the flow-rate of fluid at a given rotational rate; and the radial position of and diameters of channels leading into capillary junctions, which determines the rotational speed at which passive or capillary valving occurs. For the platform illustrated in the Figures and described herein, the assays would run identically (i.e., at the same rotational speeds) using the same component dimensions for the inner and outer ring structures. This is a consequence of the length of the mixing microchannels, which were long enough to permit substantially complete mixing to occur even through the flow-rate of fluids in the outer assay ring is higher than that in the inner ring. Additionally, the separation in rotational speed between the two capillary valving events for each assay was large enough that the sequence of fluidic motions necessary for performing the assay was obtained for both inner and outer assay rings. In alternative embodiments, the dimensions of the microfluidics components between the inner and outer rings may be different, depending on the considerations set forth herein.

In general, using identical diameters and lengths for microchannels at all radial positions may not result in equivalent performance for assay structures at those different radial positions. It is possible using the design principles of centripetally-induced fluid pumping and capillary valving (as disclosed in co-owned and co-pending U.S. Ser. No. 08/910,726, filed Aug. 12, 1997, the disclosure of which is explicitly incorporated by reference herein) to create structures that perform in similar fashion. For example, the disc may be designed such that the corresponding capillary valving events in different assay structures occur at the same rotational rate. In the example here, there are two radially-arrayed assay structures (i=1,2) that have two sequential capillary valving events in use (j=1,2). We desire the rotational speed $\omega_{11}$ to equal $\omega_{21}$ and $\omega_{12}$ to equal $\omega_{22}$. In general, for arbitrary i, j, we desire $\omega_{ij}$ is equal to $\Omega_j$ for all i, j. As disclosed in co-owned and co-pending U.S. Ser. No.; 08/910,726, filed Aug. 12, 1997, the rotational velocity at which a capillary valve bursts is $$\omega_{ij} = \frac{k}{(\langle R_{ij}\rangle \Delta R_{ij} d_{ij}^H)^{1/2}}$$

where k is a constant dependent upon the fluid density, surface tension, and contact angle of the fluid on the capillary junction; $\langle R_{ij}\rangle$ is the average radial position of the fluid radially-inward of the capillary junction; $\Delta R_{ij}$ is the radial extend of the fluid radially-inward of the capillary junction; and $d_{ij}^H$ is the hydraulic diameter of the channel used as a capillary junction (as discussed above). These three geometric variables may be manipulated to ensure that capillary valving event j occurs at the same rotational speed for all structures i. Typically, $\langle R_{ij}\rangle$ and $\Delta R_{ij}$ are somewhat constrained by placement on the disc. If, for example, identical reservoirs arrayed along the radius must gate at the same rotational speed, $\langle R_{ij}\rangle$ is proportional to the radial position; $\Delta R_{ij}$ is the same for all i; and therefore $d_{ij}^H$ must be varied inversely proportional to the radial position to maintain a constant product of the three variables, and hence the valving rotational speed.

Structure of the Assembled Microsystems Platform

Figure 6:
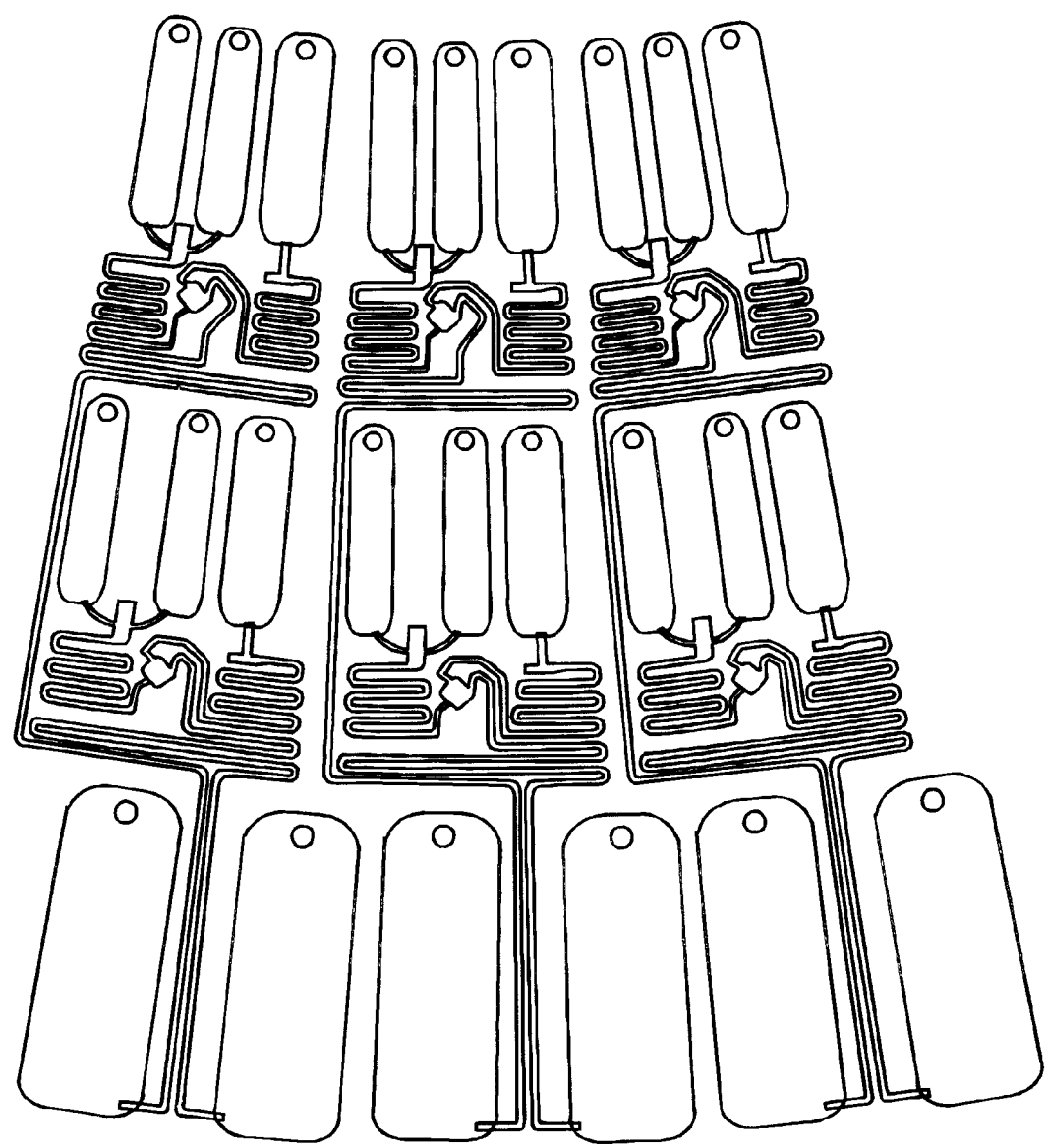
FIG. 6 is a segment of the assembled reservoir and microfluidic layers comprising the microsystems platform of FIG. 1.
Figure 7A:
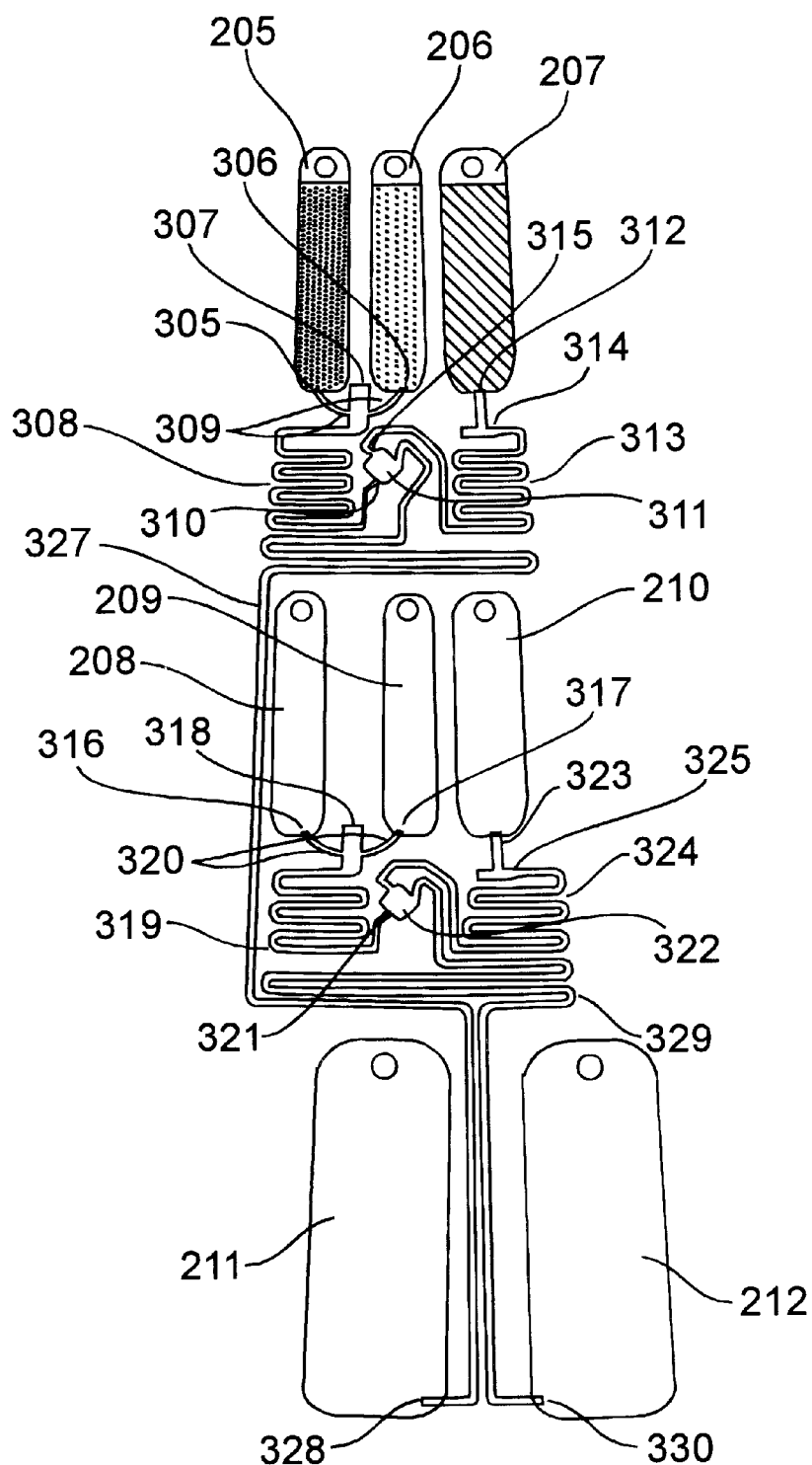
FIGS. 7a through 7f illustrate the sequence of fluid motions through a single segment of the microsystems platform comprising two microfluidic assay structures.
Figure 7B:
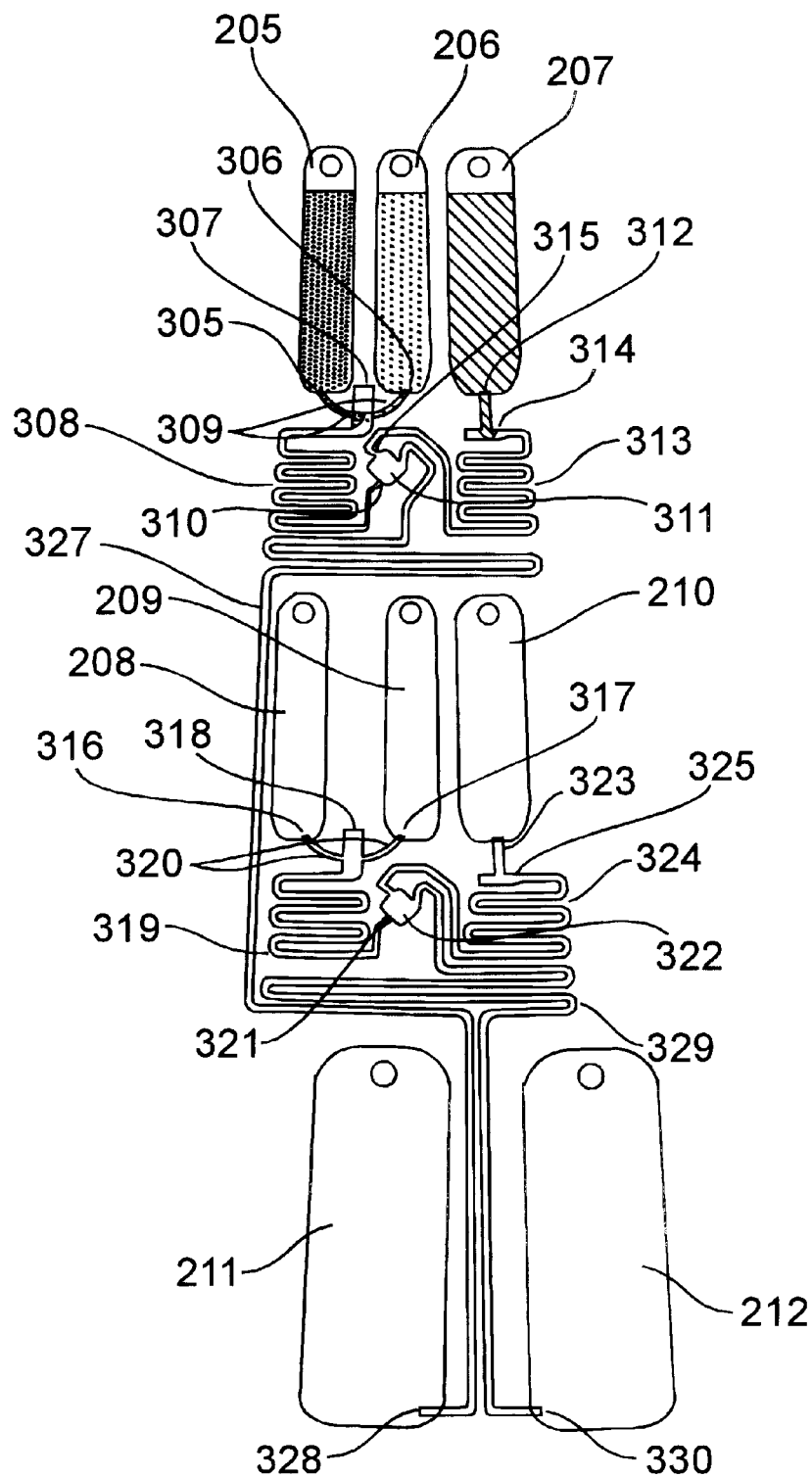
Figure 7C:
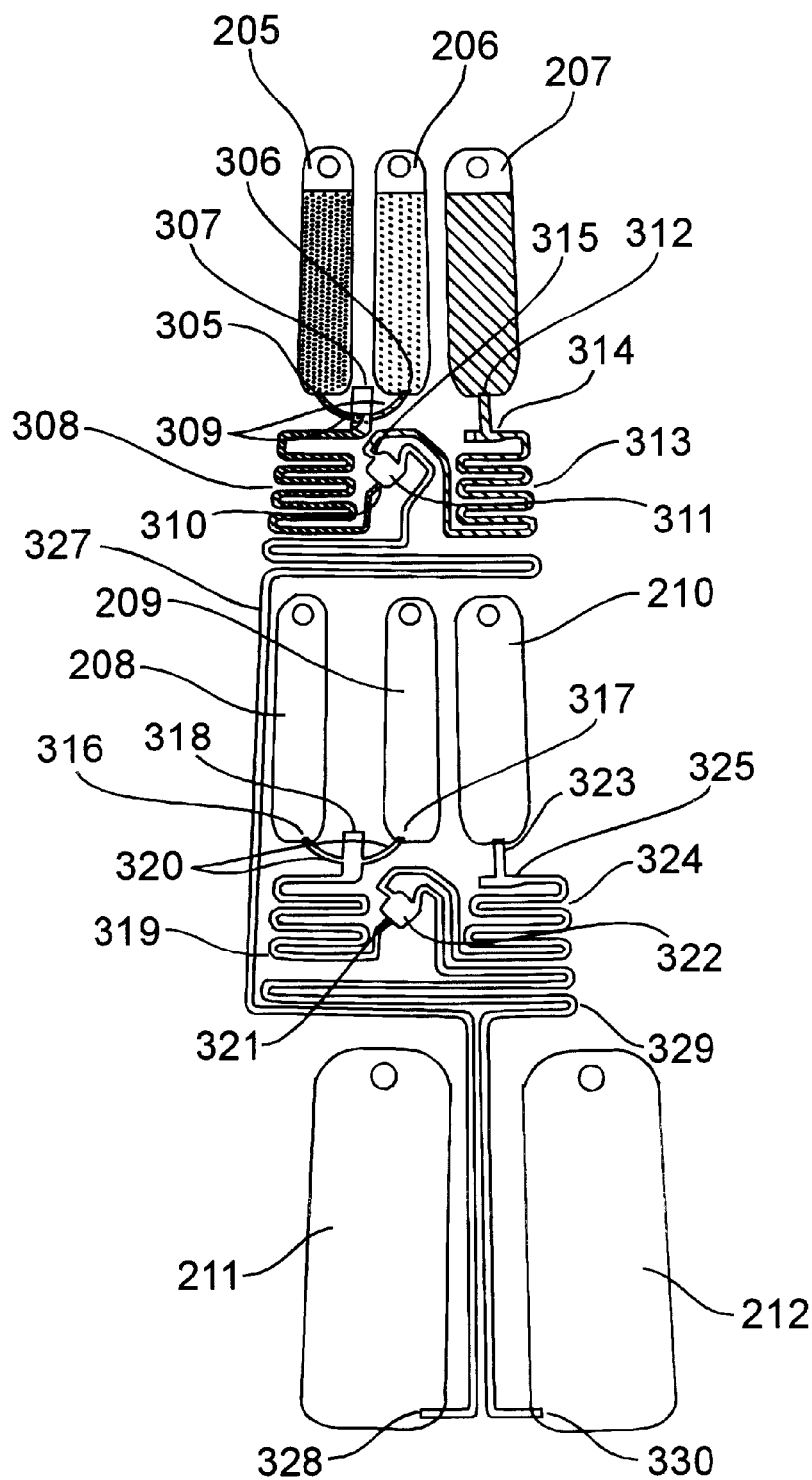
Figure 7D:
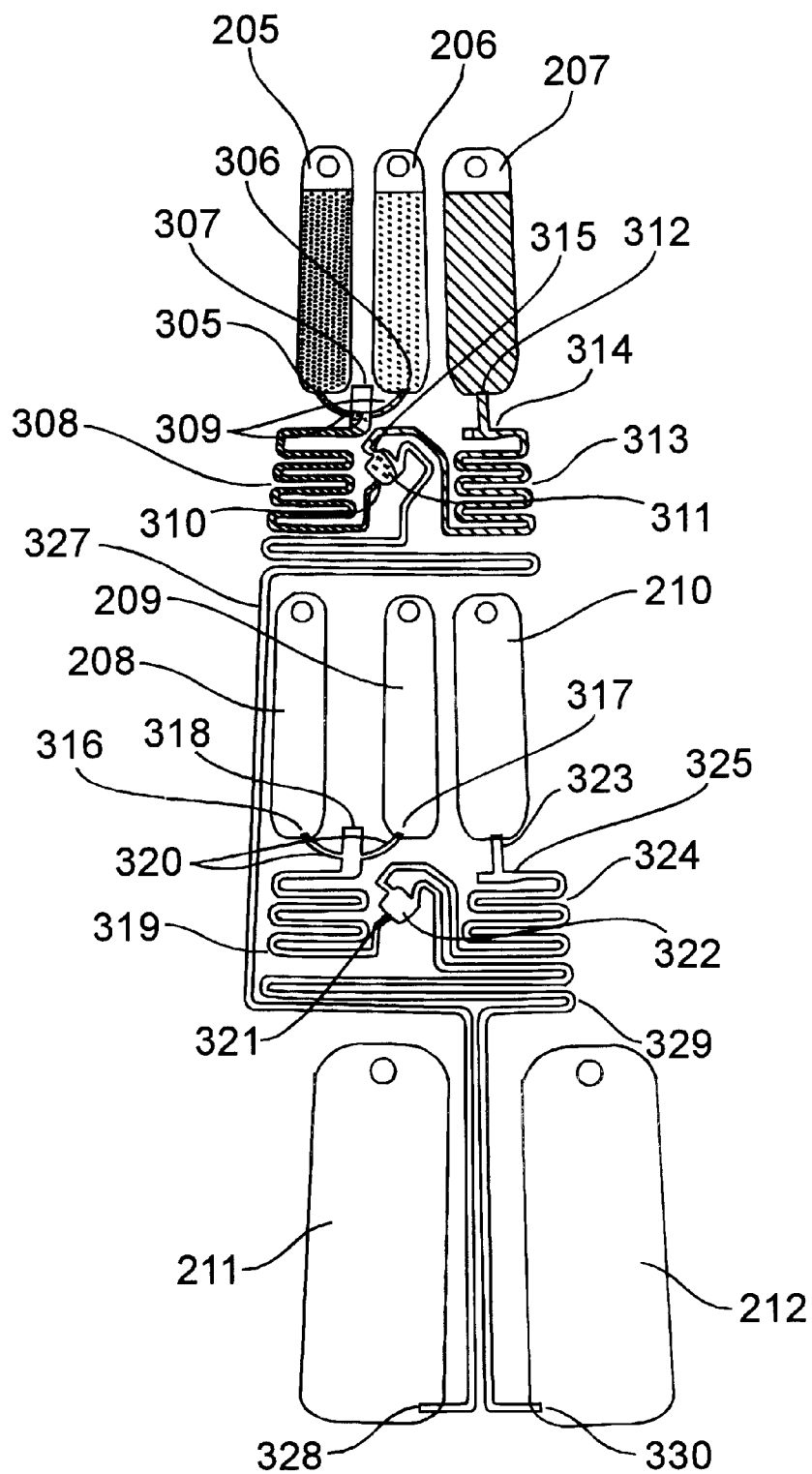
Figure 7E:
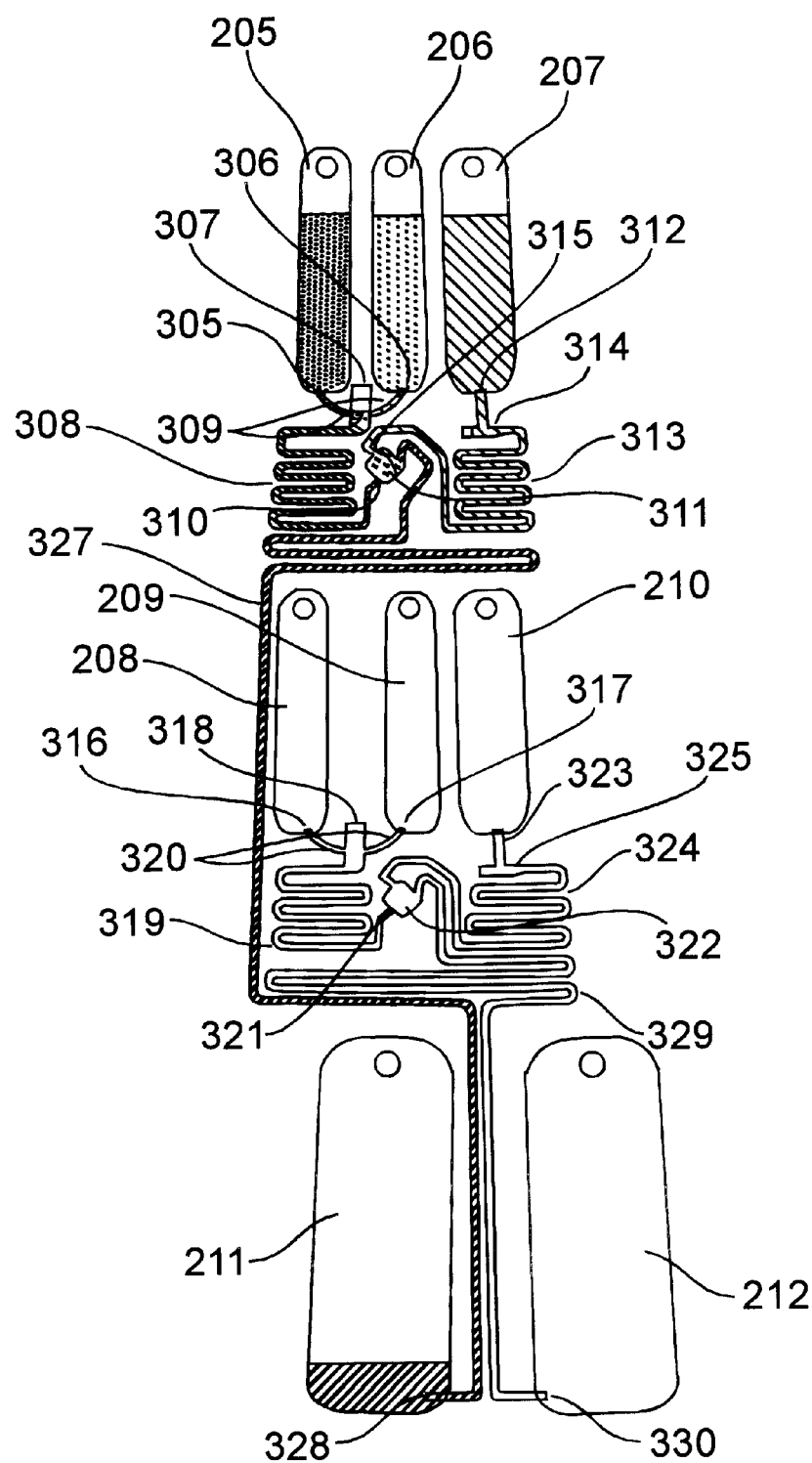
Figure 7F:
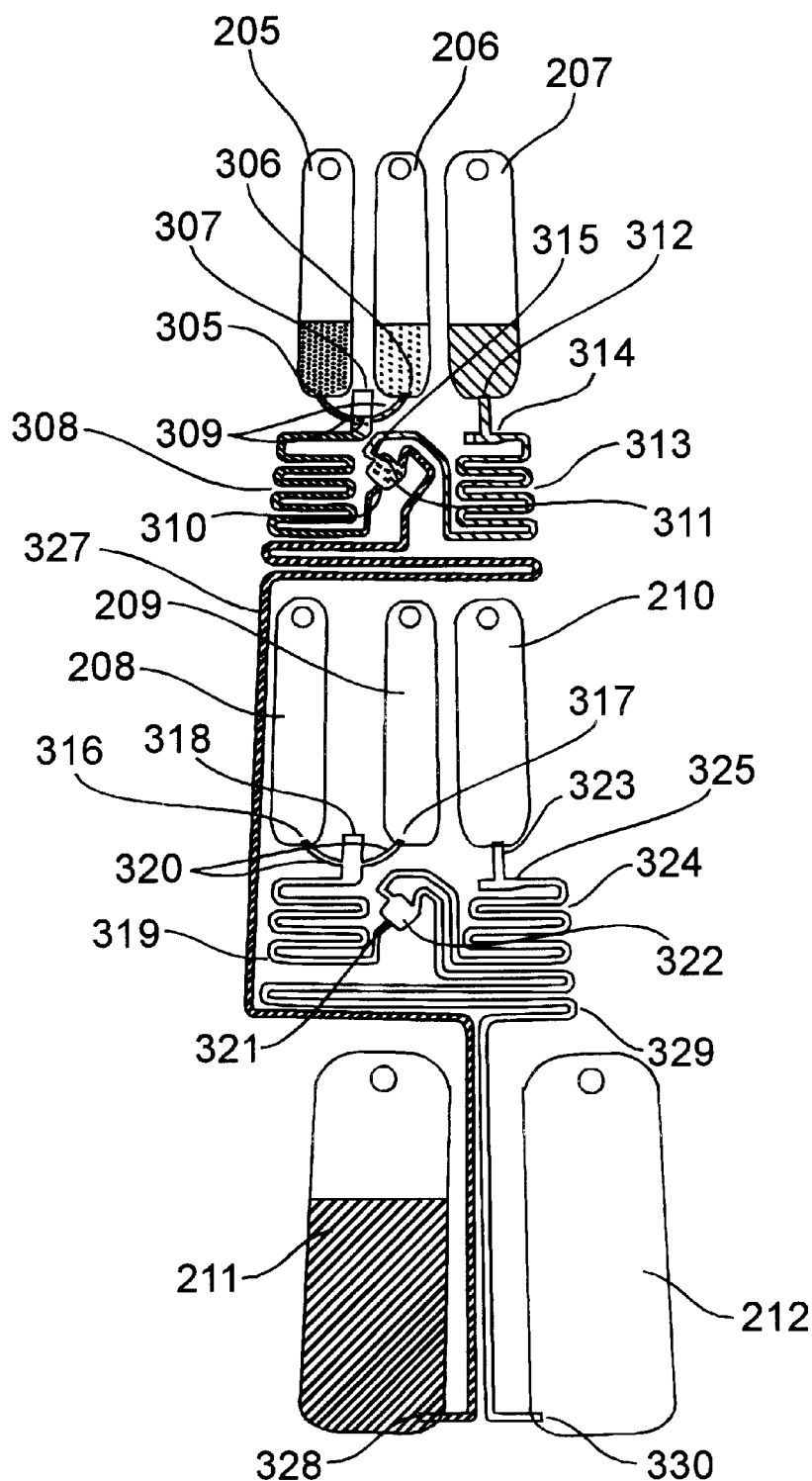

FIG. 6 illustrates three assay sectors of the assembled platform, in which the reservoirs of the reservoir layer are mated to microchannels from the microfluidics layer. The platform layers were mated as described in more detail above and in Example 1.

Because the principles by which the fluidic elements of the platforms are combined are understood, these platforms can be used for a variety of bioanalytical methods. Passive or capillary valving of two fluids to bring them into a channel and the use of that channel to facilitate fluid mixing by diffusion may be used to include any number of fluids, and is not limited to the mixture of two fluids followed by further combination of the first mixture with a third fluid, as illustrated herein. In addition, since the mixing ratios depend on the geometric shapes of the reservoirs containing the solutions to be mixed (as described more fully in co-owned U.S. Pat. No. 6,063,589, issued May 16, 2000 and incorporated by reference herein), alternative arrangements of these geometries result in mixing ratios over a large range.

Similarly, capillary valving is understood to depend on geometry, fluid properties and rotational rate, as disclosed more fully in U.S. Ser. No. 08/761,063, filed Dec. 5, 1996; U.S. Ser. No. 08/768,990, filed Dec. 18, 1996; and U.S. Ser. No. 08/910,726, filed Aug. 12, 1997, incorporated by reference herein. Alternative arrangements of the microfluidic layers of the platforms of the invention can be provided to contain any number of concentric rings of assays consistent with the amount of surface area available on the platform surface and the extent of the surface taken up by any one embodiment of microfluidics required to perform an assay.

An example of alternative platforms for performing assays of the general form disclosed herein, having a number of reservoirs whose volume is equal to the total fluid volume of an assay, VA, connected by microchannels to a collection/ detection chamber having the same volume VA. For reservoirs having a common depth, t, and microchannels and inter-assay areas occupying approximately the same area as the reagent reservoirs and collection/detection chambers, the total number of assays possible on a disc of radius R is approximately Number of assays=$\pi R^2 t/(4VA)$ For a platform having a radius of R=6 cm, a reservoir depth of 0.1 cm and a total fluid volume o12 microliters, the total number of assays that can be fit onto the disc is 235.

Other considerations include the placement of the components on the platform relative to the axis of rotation. Generally, the collection/detection chamber should he closer to the edge of the platform than the reagent reservoirs, so that there will be sufficient hydrodynamic pressure produced by convenient rotational speeds to motivate the fluid through the microchannels and mixing elements and into the collection/detection chambers. Placement of the collection/detection chambers at the outer edge of the platform also facilitates detection using a fixed optical detector. However, for extremely high-density platforms this may not be the most efficient way to arrange the assay components. For example, if the desired number of assays can be achieved only by placing the collection/detection chambers nearer the reservoirs containing the unreacted samples and reagents, it it may be necessary to use a detector that can access cuvettes at a variety of radial and azimuthal positions. An example of a scanning optical system would be one in which the optical signal is scanned radially, while the disc could be indexed beneath the optics azimuthally. In this way the optics can address any point on the disc surface. Scanning methods include a detector on a linear drive that moves radially; alternately, the optical signal may be scanned radially through the use of a galvanometrically-controlled mirror system.

A number of variations in fluidic design are possible, either dictated by assay requirements, fluidic requirements, ease-of-use or reduction in automation or all of these factors. For example, capillary valves have been shown to retain fluids in an intermediate chamber at elevated temperatures, used for incubation (as disclosed more extensively in co-owned U.S. Pat. No. 6,063,589, issued May 16, 2000, incorporated by reference). Assays that require intermediate incubations, for example, because of slow chemical kinetics, may be performed in such structures.

Alternatively, assays for which diffusional mixing is insufficient may require agitation of the fluid to effect mixing. In such a case, active valves can be used, which retain the fluids against the sudden pressure changes induced by agitation, as described in more fully in co-owned and co-pending U.S. Ser. No. 09/315,114, filed May 19, 1999.

It may also be desirable to treat the platform surfaces to change the liquid contact angle for controlling capillary valving properties, as disclosed in co-owned and co-pending U.S. Ser. No. 08/910,726, filed Aug. 12, 1997, incorporated by reference.

The following Examples are intended to further illustrate certain preferred embodiments of the invention and are not limiting in nature.

EXAMPLE 1

Simultaneous Enzyme Inhibition Assays

A platform as depicted in the Figures was prepared as follows. The reservoir layer was manufactured through machining of acrylic using computer/numerical code machining using a Light Machines VMC5000 milling machine running Light Machines "Benchman" software (Light Machines Corporation, Manchester, N.H.).

The microfluidics layer was manufactured as follows. A microfluidics structure such as the structure shown in FIG. 5 was designed using in a computer aided design package such as AutoCAD (Autodesk, San Rafael Calif.) and Freehand (Macromedia Inc., San Fransisco, Calif.). This design was converted into a photomask by printing at high resolution (3386 dpi) on a transparent plastic sheet. A 125-mm diameter silicon wafer was coated with a layer of negative photoresist (SU-8(50)) and spun on a spin-coater (obtained from Chemat Technology, Northridge, Calif.) at a speed sufficient (200 to 8000 rpm) to give a desired thickness between 5 $\mu$m and 500 $\mu$m. The silicon wafer was baked to have a smooth surface and then the photoresist partially cured. The silicon wafer was exposed to ultraviolet (UV) light using a conventional UV source and mask aligner. The photoresist was then developed in propylene glycol methyl ether acetate and non-crosslinked photoresist removed through washing in dichloromethane. The resulting relief was then passivated by exposure to a vapor of tridecafluoro-1,1,2,2-tetrhydrooctyl-1-trichlorosilane and used as a mold for microfabrication (as described in Duffy et al., 1998, Anal. Chem. 70: 4974–4984).

A 10:1 mixture of polydimethylsiloxane (PDMS) oligomer and crosslinking agent (Sylgard 184, Dow Corning) was poured onto the mold after degassing under vacuum. PDMS is a clear material; by adding 1 wt % liquid pigment, the disc was made white for reflectance optical measurements or black for fluorescence measurements. The poured elastomer was then cured at 65° C. for 1 hour. The resulting microfabricated PDMS part was peeled from the mold. The mold could then be re-used to fabricate additional copies of the microfluidics layer.

The microplatform was assembled by forming a reversible, conforming seal between the PDMS microfluidics layer and the acrylic reservoir layer made through simple physical contact of the two components. This seal is based on physical adhesion forces alone—van der Waals attraction forces and potentially static electrical charge present on the surfaces—and was sufficient to seal the disc against leakage due to the centripetally-induced pressures used.

The platform shown in FIG. 1 and prepared as described herein was used to perform simultaneously and in parallel ninety-six enzyme inhibition assays, in order to demonstrate that the microfluidics platforms of the invention provide an alternative to enzyme assays performed in conventional 96-well microtitre plates. Fluids were deposited in the reservoirs formed in reservoir layer 201 when reservoir layer is mated or bonded with microfluidics layer 301. Platform 100 was then rotated using a rotational profile designed to drive fluids through the microchannels within microfluidics disc 301.

The platform shown in FIGS. 1 through 6 was used to perform 96 simultaneous enzyme inhibition assays as model homogeneous assays. In an enzyme inhibition assay, the effect of a compound present in a first fluid ("A") upon the capacity of an enzyme present in a second fluid (fluid "B") to catalyze a reaction, typically of a substrate in a third fluid ("C") is determined. The reaction was chosen to give a change in a readily-measured parameter of the fluid, such as its optical density, or to produce a fluorescent moiety. When no inhibitor was present in fluid A, mixing solution A with enzyme solution B had no effect: enzyme activity detected in this assay was the maximum detected and provided the largest change in the measured parameter. However, if an inhibitor was present in fluid A, mixing fluid A with fluid B resulted, after a sufficient time in a chemical reaction or other change induced by the inhibitor in most or all of the enzyme molecules, rendering them incapable of catalyzing the desired reaction. If this solution was mixed with the substrate solution, little or no change in the measured parameter was seen.

The system chosen to model homogeneous assays consisted of theophylline as inhibitor, alkaline phosphatase as the enzyme, and p-nitrophenol phosphate (PNPP) as the substrate. In the presence of alkaline phosphatase, PNPP, which is colorless, is converted to p-nitrophenol (PNP), which absorbs in the blue portion of the visible light spectrum and therefore appears yellow. Theophylline was used in concentrations of 0.01 mM to 100 mM to provide a standard dose-response curve in the inhibitor. Alkaline phosphatase was used in a 1 mg/mL solution, and PNPP was used as a 0.5 mM solution. All solutions were made in a buffer of 0.1M glycine and 0.5 mM $MgCl_2$ in deionized water.

The dimensions of the platform used for these assays were as follows. The overall platform diameter was 12 cm. The reservoir layer was about 3.2 mm thick. The radial positions of the ends of reservoirs 205, 206, and 207 most proximal to the center of the disc were about 3.25 cm and will be denoted as "inner radii;" the radial positions of the ends 205, 206, and 207 most distant from the center of the disc were about 3.7 cm and will be denoted "outer radii." Reservoirs 205, 206 and 207 were about 1.2 mm deep. The angle subtended by each reservoir was chosen such that it could accommodate appropriate volume. Reservoirs 205 and 206 subtended angles of about 1.6 degrees, while reservoir 207 subtended an angle of about 2.1 degrees such that reservoirs 205 and 206 could accommodate a 3 $\mu$L volume and reservoir 207 accommodated a 6 $\mu$L volume. For the outer reservoirs, 208, 209 and 210, the inner radii were about 4.1 cm, the outer radii were 4.5 cm, and the platform was about 3.2 mm thick. Reservoirs 208 and 209 subtended angles of about 1.25 degrees and reservoir 210 an angle of about 1.7 degrees such that they could accommodate 3 $\mu$L and 6 $\mu$L, respectively. Detection chambers 211 and 212 were constructed of optically-transparent material and had an outer radius of about 5.7 cm and an inner radius of about 5 cm, were 1 mm deep, and had a subtended angle of 2.7°.

The microfabricated layer was also 12 cm in diameter and had a thickness between 1 and 5 mm (although the thickness is not important) and was composed of white PDMS. The depth of all microfluidic structures (that was determined by the height of the SU-8 relief) was 100 $\mu$m. The width of mixing microchannels 308, 313, 327, 319, 324 and 329 was 100 $\mu$m. The lengths of the mixing microchannels was chosen to provide sufficient time for mixing via diffusion with liquids of moderate diffusion constant ($8\times10^{-6}$ $cm^2/s$) as fluids were pumped through them under the influence of centripetal acceleration. These lengths were about 15 mm for mixing microchannels 308 and 313, about 36 mm for mixing microchannel 327, about 14 mm for mixing microchannels 319 and 324, and about 29 mm for mixing microchannel 329. These dimensions resulted in the fluids taking $\geq$2 sec to transit the mixing microchannels.

Fluid flow was controlled on the platforms by capillary valving as described in co-owned U.S. Pat. No. 6,063,589, and co-owned and co-pending U.S. Ser. No. 08/761,063, filed Dec. 5, 1996; U.S. Ser. No. 08/768,990, filed Dec. 18, 1996; and U.S. Ser. No. 08/910,726, filed Aug. 12, 1997 incorporated by reference. For each inner assay microfluidics structure, there were four capillary valving points: at the junction of microchannels 305 and 306 with microchannel 307; at the junction of microchannel 312 with microchannel 314; at the junction of constriction 315 with capillary junction 311; and at the junction of constriction 310 with capillary junction 311. The widths of the channels leading into the junctions was 100 $\mu$m for microchannels 305 and 306; 200 $\mu$m for microchannel 312; and 50 $\mu$m for capillary junctions 310 and 315. For the outer assay arrays, the corresponding microchannels have identical widths at those junctions as for the junctions in the inner assay arrays (100 $\mu$m for microchannels 316 and 317; 200 $\mu$m for microchannel 323; and 50 $\mu$m for capillary junctions 321 and 326.

The assays were run as follows. 3 $\mu$L aliquots of alkaline phosphatase and theophylline solutions having the concentrations set forth above were loaded into reservoirs 205 and 208 (alkaline phosphatase) and 206 and 209 (theophylline). 6 $\mu$L aliquots of PNPP solution were loaded into reservoirs 207 and 210. The platform was placed on the spindle of an instrument containing a diffuse reflectance optical head capable of three-color measurements. The platform was first rotated at 750 rpm for 10–30 seconds in order to "prime" the microchannels 305, 306, 312, 316, 317, and 323 (i.e., to pump the fluid into the microchannels to the point where they were retained at the enlargements forming the capillary junctions). The rate of rotation was then increased at an acceleration rate of 45 rpm/sec to a rotational speed of 840 rpm. At this rotational rate, the pressure induced by centrifugation at capillary junctions 309, 314, 320 and 325 is sufficient to overcome the capillary pressure and fluids entered channels 308, 313, 319 and 324. The rotational rate of 840 rpm was maintained for 30 seconds (though in practice this could be reduced as low as a few seconds), during which time fluids traversed the channels to the capillary junctions at 310, 315, 321 and 326, where they were retained due to capillary pressure. The rotational rate was then increased at an acceleration rate of about 180 rpm/sec to a rotational speed of 1200 rpm and maintained there for 1 sec. At this rotation rate the fluids burst past the capillary junctions at 311 and 322 and entered microchannels 327 and 329. The rotational velocity was then reduced to 600 rpm at a rate of 150 rpm/s and maintained for 50 seconds to effect pumping of the fluids into the detection chambers 211 and 212.

FIGS. 7a through 7f illustrate the sequence of fluid flows. At 840 rpm, fluid began to flow from reservoirs 205, 206 and 207 and was halted at constriction 310. Similarly, the substrate solution flowed from 207 to constriction 315. If either the fluid in 205 or 206 flowed into 307 and 308 first, the narrowness of the channel 308 provided sufficient resistance that fluid the fluid accumulated in expansion area 307, thereby wetting the protruding liquid interface of the opposite channel. In this way both fluids are guaranteed to be brought into contact and into the microchannel together.

In alternative embodiments, the diameters of the capillary junctions x and y may be chosen to pre-dispose one or the other of the fluids to flowing at a lower rotational rate. For example, if there is variability in the surface tension of one fluid because of compositional variations (for example, if it is a biological fluid), it may be desirable to effect the motion of the other fluid first. In this case the capillary junction of the variable fluid is made narrower in a way to insure that the capillary valving rpm for all reasonable variations in fluid properties is higher than that of the other fluid.

The fluids then moved through the microchannels and were retained at constrictions 310 and 315. At rotational speeds between 840 rpm and 1200 rpm, either the fluid from the alkaline phosphatase/theophylline mixture or the substrate solution, or both, burst through capillary junction 311. Because of the design of capillary junction 311, whichever fluid flows first is forced to wet the exit capillary of the other fluid, thereby inducing it to flow into microchannel 327 as well.

An important feature of mixing in the device is made possible through the narrowness of microchannels 308, 313, and 327. The resistance to flow due to rotationally-induced pressure of a channel that is denoted by $R_H$ is given by $$Q = \frac{P}{R_H}$$

$$R_H = C \frac{l}{(d^H)^4}$$

where Q is a flow-rate, P is the induced pressure, C is a constant, l is the length of the channel through which the fluid flows and $d^H$ is the hydraulic diameter. Because the diameter of microchannels 308, 313, and 327 are much narrower than that of the reservoirs 205, 206 and 207, the resistance to flow is dominated by the microchannels, and hence the pressure drop across the flowing fluid is sustained almost exclusively over the length of the mixing microchannels. This insures that the fluids flowing from feed reservoirs into mixing channels do so in a strict, known ratio. In particular, assume that fluid begins to flow from one reservoir into the mixing channel at a rate faster than the fluid flows from the other reservoir. The resulting pressure drop from the meniscus of the fluid at the inner edge of the reservoir to the point where the fluids mix for the fluid that flowed faster will be less than that of the other fluid, because the rotationally-induced pressure is proportional to the radial extent of the fluid (ΔR discussed earlier). Because a higher pressure now exists across the fluid that moved more slowly, it is induced to flow more rapidly. This process of feedback provides a pressure-equalization phenomenon that results in the inner meniscuses of fluids in reservoirs 205, 206 and 207 progressing outward at the same radial velocity (same distance in the radial direction per unit time). As a result, the ratio of the alkaline phosphatase and theophylline flow-rates as a function of time in mixing microchannel 308 is given exactly by $$\frac{Q_A}{Q_B}(t) = \frac{A_A}{B_B}(t)$$

where $A_A$ and $B_B$ are the cross-sectional area of the reservoirs 205 and 206 as a function of time, or alternately, radial position of the meniscus as fluid is removed from the reservoirs. If it was desired that the ratio of flows is constant (as was the case here), it was sufficient to maintain a constant ratio of cross-sectional areas as a function of radial position. Note that this does not imply that the cross sections are constant, just that their ratio is. The ratio expressed in the equation can be manipulated by altering the ratio of cross-sectional areas of the reservoirs, as disclosed more fully in co-owned U.S. Pat. No. 6,063,589, issued May 16, 2000 and incorporated by reference.

This equation and analysis also accurately describes the significance of the ratio of the three fluids in mixing microchannel 327. As the fluid enters mixing microchannel 327, the pressure induced by rotation works against the hydraulic resistance to flow the reservoirs 205, 206, and 207; the hydraulic resistance of the channels 308, 313, and 319; and the mixing microchannel 327. Because the lengths and diameters of 308, 313, and 319 are chosen to be identical, the hydraulic resistance across these channels are identical as well. As a result, the hydraulic resistance of mixing microchannel 327 and the reservoirs 205, 206, and 207 are the determining factors for the relative flow-rates of the fluids. Again, because the resistance of the microchannel 327 is much greater than that of the reservoirs due to its much smaller diameter, the pressure-equalization phenomenon described above again results in meniscuses for all three fluids that move from the inner portion of the reservoirs to the outer portion as fluid is drained. In this way, alkaline phosphatase and theophylline solutions enter microchannel 308 as co-flowing laminar streams. Because microchannel 308 is long and the flow rates are controlled by rotational rate, these co-flowing streams are present for a time long enough for diffusion across the interface between these streams to effect complete mixing of the solutions. Similar statements may be made about fluid flow in microchannel 327.

This description of fluid flow and mixing applies to both the "inner ring" set of assay microfluidics structures and to the "outer ring" of such structures.

After fluid was delivered to the detection chambers 211 and 212, reflectance optics was used to measure the reflected radiation at an off-specular (diffuse) angle at two wavelengths, 430 nm (absorbing for the expected reaction product, PNP) and 630 nm. As there is no absorbance from reaction product PNP at 630 nm, this wavelength can be used to correct for optical imperfections in the platform, stray scattering, or unintended air bubbles in the optically-transparent chamber. The optical system also advantageously contained a beam-splitter that sent a fraction of the incident light to a reference photodiode. Two detectors used in this optics system were the assay detector, which measured diffusely-reflected light; and the reference detector, which measured a fraction of the incident light. Measurements at each detector were made when both the 430 nm and 630 nm light sources were active as well as when they were "dark" or off. The measured voltages were thus:

$V_D^D$ dark measurement in assay detector $V_R^D$ dark measurement in reference detector $V_D^1$ measurement at absorbing wavelength $\lambda_1$ (430 nm) in assay detector $V_D^2$ measurement at non-absorbing wavelength in $\lambda_2$ (660 nm) assay detector $V_R^1$ measurement in reference detector at absorbing wavelength $\lambda_1$ (430 nm)

$V_R^2$ measurement in reference detector at non-absorbing wavelength $\lambda_2$ (660 nm)

The absorbance at 430 nm is calculated from $$K = \frac{\left(\frac{V_D^1 - V_D^D}{V_R^1 - V_R^D}\right)}{\left(\frac{V_D^2 - V_D^D}{V_R^2 - V_R^D}\right)}$$

$$A = -\log(K) C_{PNP}$$

Here, $C_{PNP}$ is the concentration of yellow product, p-nitrophenol; this concentration is inversely related to the concentration of theophylline in the initial solution.

Figure 8:
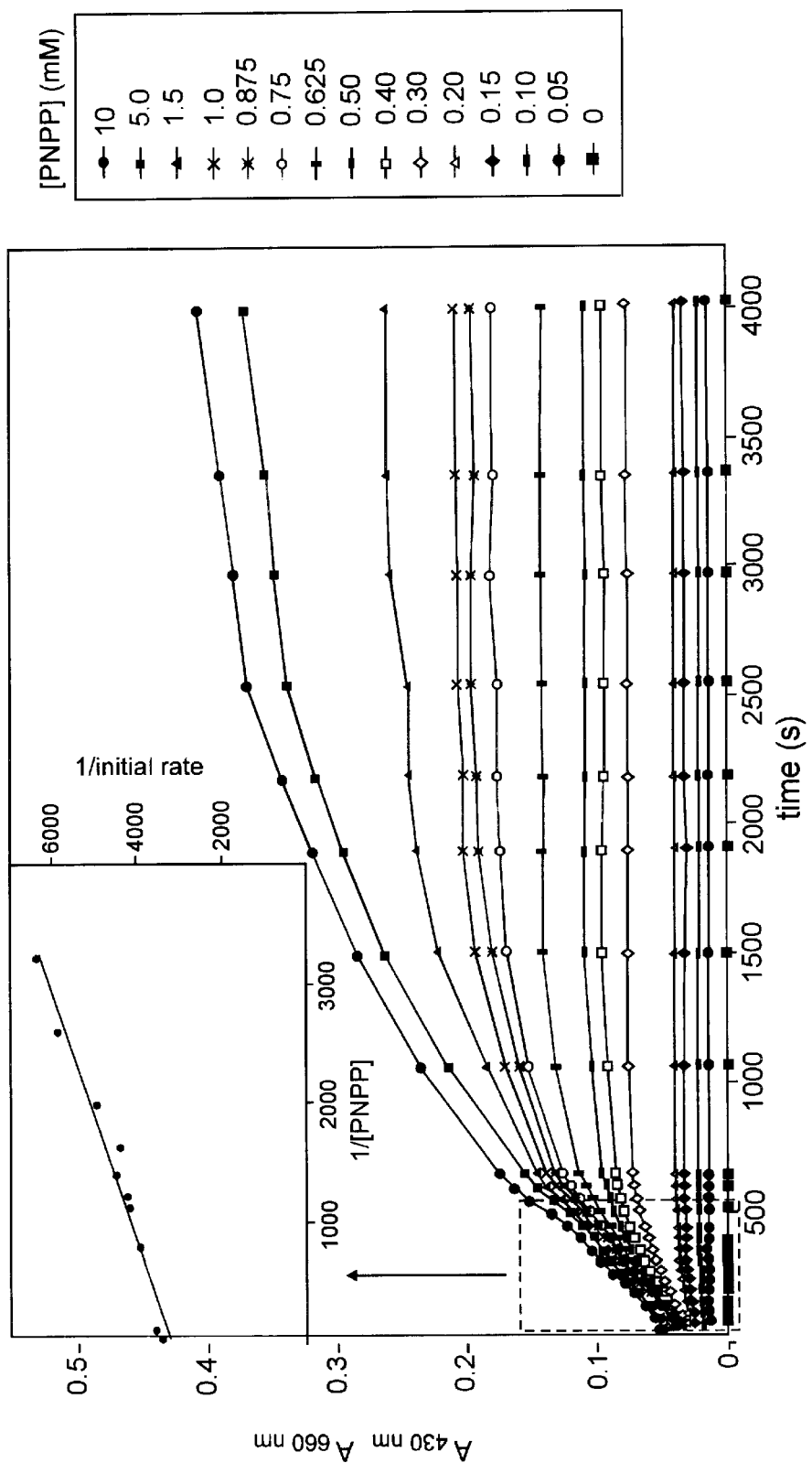
FIG. 8 illustrates kinetic data for enzymatic inhibition assays performed with the devices of the invention.

Data was collected continuously as the platform was rotated at 60 or 100 rpm. Because data can be taken continuously, the kinetics of the chemical reactions could be observed. FIG. 8 shows data for 48 assays run simultaneously on the platform, representing three-fold replicates for each of fifteen theophylline concentrations ranging from 0 to 10 mM. By analyzing the linear fit of the data as a function of time to the assurance for each assay between 0 and 500 s, kinetic information can be extracted. Michaelis-Menton analysis (Lehninger, 1975, *Biochemistry*, $2^{nd}$ Ed., Worth: N.Y.) yields a Michaelis constant, $K_m=(0.27\pm0.02)\times 10^{-3}$ M. This value is the same order of magnitude as those determined for alkaline phosphatase in similar assay systems (Foulds et al., 1990, in *Biosensors: A Practical Approach*, Cass, ed., Oxford University Press: Oxford, U.K, pp. 97–124).

Figure 9:
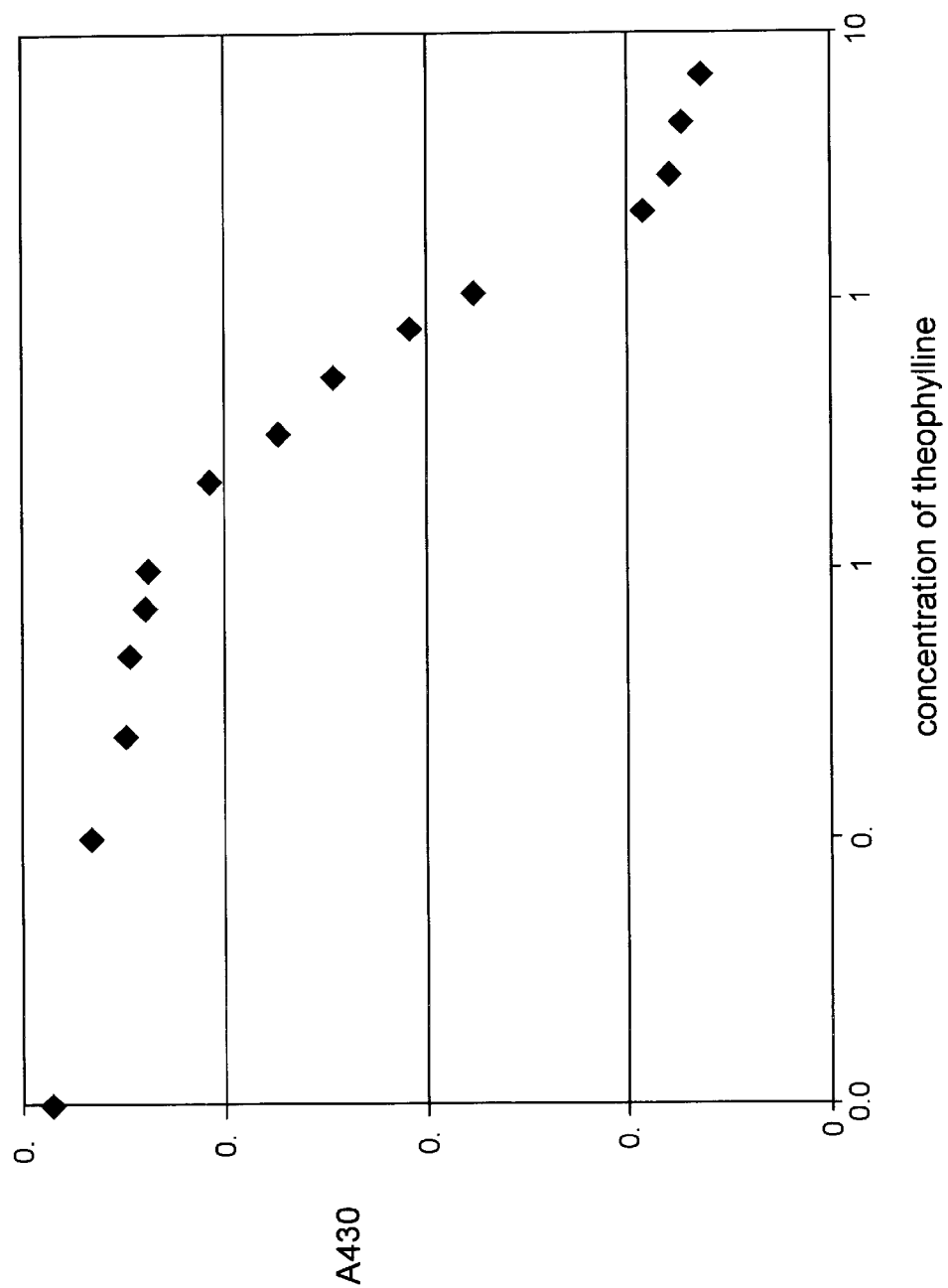
FIG. 9 is a dose-response curve illustrating enzymatic activity as a function of inhibitor concentration for enzymatic inhibition assays performed with the devices of the invention, as disclosed in Example 1.

End-point analysis is also possible by choosing a time—here, 2 minutes—after the fluid is pumped into the detection chambers for the obtaining optical data. FIG. 9 shows the end-point measurement (dose-response curve). By fitting this data to a Langmuir isotherm, an inhibition constant of $(9.7\pm0.9)$mM was determined. For these data, the coefficients of variation are approximately 3 to 3.5%, of which approximately 1.5% was due to instrumentation and disc variations, as determined through analysis of known concentrations of pre-mixed reagents or dyes.

These results demonstrated that microplatform systems according to the invention can be used as a substitute for conventional 96-well microtitre plates for performing enzyme assays to determine enzymatic activity thereof.

EXAMPLE 2

Tryspin Assay

A further type of homogeneous assays used in high-throughput drug screening are serine protease assays. Interest in these enzymes derives from their implication in a wide variety of normal and pathologic metabolic conditions. Serine proteases include:

Most of the factors involved in the coagulation pathways that create blood clots.

The enzyme cascade that digests blood clots.

Several components of the complement system, that mediates the inflammatory response, promote the phagocytization of foreign matter, and lyses infective cells.

Major components of the intracellular processing of proteins.

Major destructive products of several viruses.

Active factors in digestion.

Members of the acute phase reactant response to inflammation.

Much current serine protease high throughput screening (HTS) research involves the regulation of the body's reaction to inflammation. For instance, when an infection occurs or tissue is dead or damaged, neutrophils release human leukocyte elastase, cathepsin G and various proteinases to initiate the degradation of foreign materials. Unfortunately, many chronic diseases, including emphysema, chronic bronchitis, cystic fibrosis, pancreatitis, arthritis, and periodontitis, create abnormal inflammation that activates this neutrophil response. The continuous release of serine proteases overwhelms the body's natural regulatory mechanisms, and tissue damage is increased. However, because of the ubiquity and importance of these molecules, specific enzyme inhibitors are needed.

An exemplary serine protease is trypsin. It is a vital part of intercellular metabolism but is released when cells lyse. Its proteolytic activity is so potent that animals produce a constitutive inhibitor, $\alpha_1$-antitrypsin ($\alpha_1$-AT), that is maintained at significant blood levels, even pre-natally. A number of genetic mutations that reduce or eliminate ($\alpha_1$-AT activity in the blood have been identified. An estimated 10% of the U.S. population is heterozygous or homozygous for one of these mutations. Even the heterozygous population is prone to chronic liver and lung diseases. In addition, chronic inflammation releases trypsin levels that help to overwhelm the body's ability to make extra $\alpha_1$-AT in heterozygous normal individuals.

The platform described in Example 1 was used to demonstrate a model assay for a trypsin inhibitor, ovomucoid inhibitor.

Contrasting manual performance of this assay with the assay as performed using a microsystems platform of the invention, manual performance requires: mixing of trypsin with ovomucoid inhibitor; incubation at 37° C. for 30 minutes; mixing of first fluid mixture with substrate BODIPY FI (casein substrate); and fluorescence detection.

The assay was performed on the bench using the above protocol. Trypsin was used at a concentration 50 µg/mL. Ovomucoid inhibitor was used in the ranges of 0–50 µg/mL. The fluorescent substrate BODIPY FI was used in a concentration of 33 µg/mL. These three fluids were combined in volumes of 3 µL, 3 µL, and 6 µL, respectively. This substrate yields a fluorescent peak at 520 nm when it has been cleaved by trypsin. Incubation was performed using a standard laboratory incubator. The fluid was then transferred into the detection cuvettes of the disc described above. The disc was placed on an epiflourescence microscope with a band-pass filter centered at 520 nm. The disc was indexed beneath the objective of the microscope and the fluorescent signal measured.

The assay was then performed on the disc of the invention using the concentrations and volumes described above. In reference to the previous example, trypsin takes the, place of alkaline phosphatase, ovomucoid inhibitor takes the place of theophylline, and BODIPY FI (casein substrate) takes the place of PNPP. The rotational profile used to effect fluid motion is as described above. Here the 37° C. incubation is replaced by about a 10 sec mixing in the first mixing channel before the solution is brought into contact with the substrate.

Figure 10A:
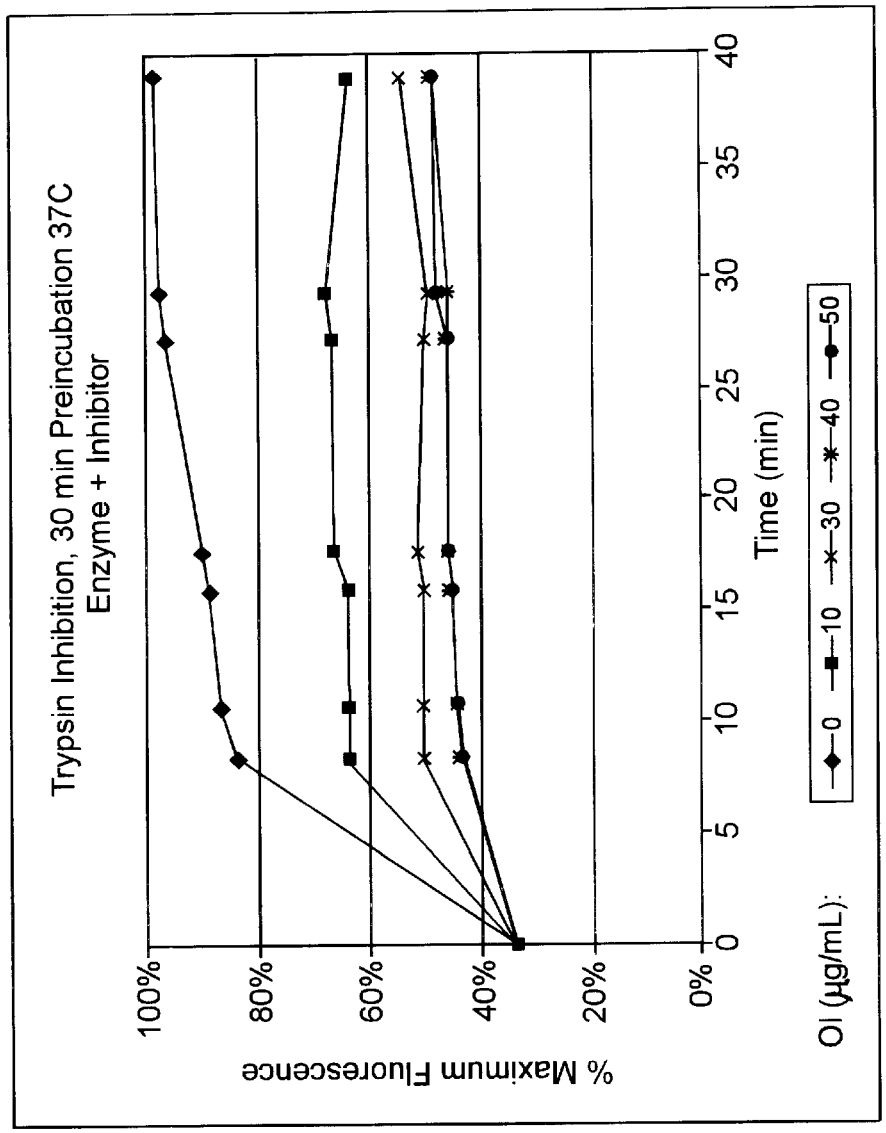
FIGS. 10a and 10b is another dose-response curve illustrating enzymatic activity as a function of inhibitor concentration for for enzymatic inhibition assays performed with the devices of the invention, as disclosed in Example 2.
Figure 10B:
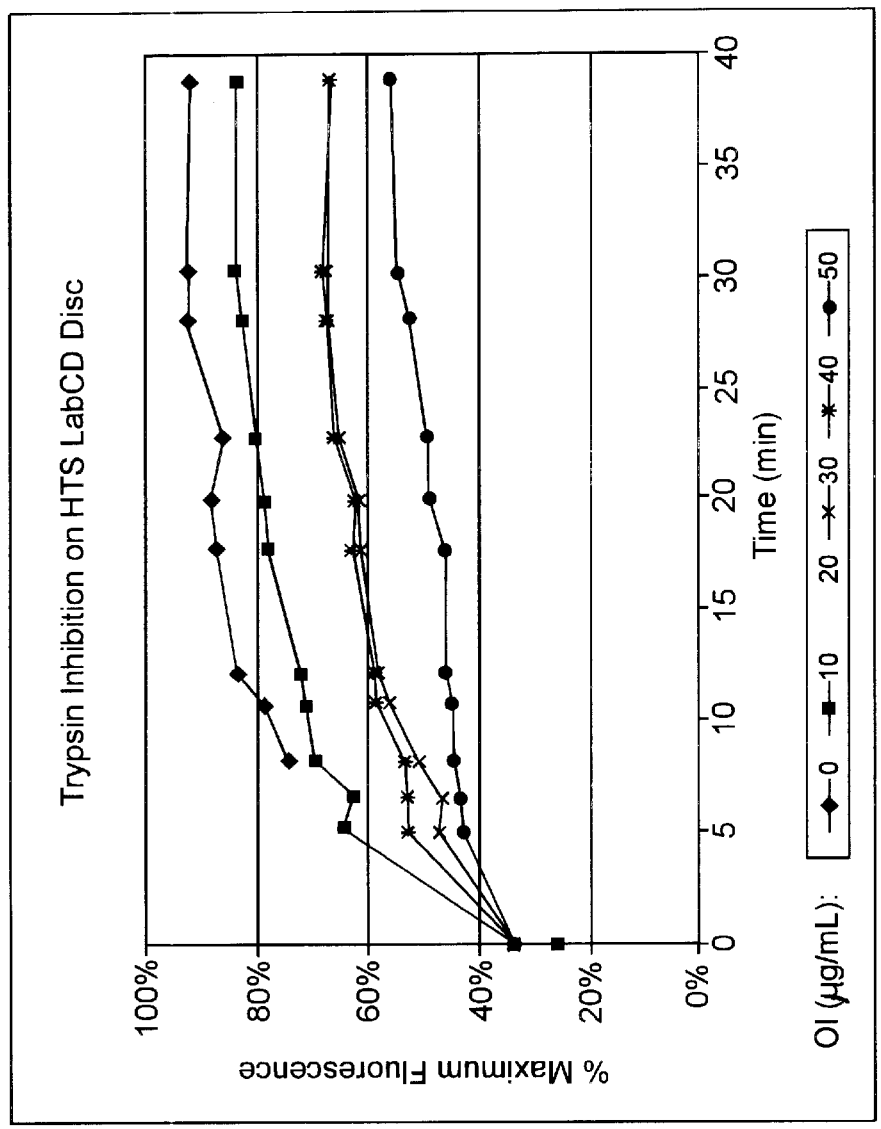

FIGS. 10*a* and 10*b* show both the using the disc and instrument of the invention. These data show comparable performance on-disc for relevant concentrations of ovomucoid inhibitor, 0–50 µg/mL, even in the absence of the incubation step.

It should be understood that the foregoing disclosure emphasizes certain specific embodiments of the invention and that all modifications or alternatives equivalent thereto are within the spirit and scope of the invention.

What is claimed is:

1. A centripetally-motivated microsystems platform comprising:
    a) a rotatable platform comprising a substrate having a surface comprising one or a multiplicity of microfluidics structures embedded in the surface of the platform, wherein each microfluidics structure comprises
        i) one or a plurality of reagent reservoirs containing a reagent solution
        ii) one or a plurality of sample reservoirs containing a sample solution,
        iii) a mixing microchannel, wherein each mixing microchannel is fluidly connected to a sample reservoir and one or a plurality of reagent reservoirs by a microchannel, and
        iv) a collection chamber fluidly connected to the mixing microchannel by a microchannel, wherein the mixing microchannel defines a longitudinal path in the surface of the platform, the mixing microchannel being configured to bend a plurality of times around a plurality of curves as it traverses the longitudinal path on the platform, the longitudinal path having a length sufficient to mix the sample solution and the reagent solutions to a homogenous mixture, and wherein fluid within the microchannels of the platform is moved through said microchannels by centripetal force arising from rotational motion of the platform for a time and a rotational velocity sufficient to move the fluid through the microchannels.

2. A microsystem platform of claim 1 wherein each sample reservoir further comprises a sample input port.

3. A microsystem platform of claim 1 wherein each reagent reservoir further comprises a reagent input port.

4. A microsystem platform of claim 1 wherein each collection chamber further comprises a fluid outlet port.

5. A microsystem platform of claim 1 wherein the collection chambers are optically transparent.

6. A microsystem platform of claim 1 wherein each sample reservoir has a volumetric capacity of from about 1 nL to about 500 μL.

7. A microsystem platform of claim 1 wherein each reagent reservoir has a volumetric capacity of from about 1 nL to about 500 μL.

8. A microsystem platform of claim 1 wherein each collection chamber has a volumetric capacity of from about 2 nL to about 1000 μL.

9. A microsystem platform of claim 1 wherein each mixing microchannel comprises a plurality of bends having angles greater than 90°.

10. A microsystem platform of claim 1 comprising from about 24 to about 10,000 microfluidics structures.

11. A microsystem platform of claim 1 wherein rotation of the platform motivates fluid through each of the microfluidics structures at a flow rate wherein the time the fluid is in the mixing microchannel is substantially the same in each of the microfluidics structures on the platform.

12. A microsystem platform of claim 11 wherein the flow rate of fluid through each of the microfluidics structure is from about 1 nL/s to about 100 μL/s.

13. A microsystem platform of claim 11 wherein the flow rate of fluid through each of the microfluidics structure is from about 1 nL/s to about 500 μL/s.

14. A microsystem platform of claim 1 that is a circular disk.

15. The microsystem platform of claim 1, wherein the microsystem platform is constructed of a material selected from the group consisting of an organic material, an inorganic material, a crystalline material and an amorphous material.

16. The microsystem platform of claim 15, wherein the microsystem platform further comprises a material selected from the group consisting of silicon, silica, quartz, a ceramic, a metal or a plastic.

17. The microsystem platform of claim 14, wherein the microsystem platform is a circular disk having a radius of about 1 to about 25 cm.

18. The microsystem platform of claim 1, wherein the microsystem platform has a thickness of about 0.1 to 100 mm, and wherein the cross-sectional dimension of the microchannels embedded therein is less than 500 μm and from 1 to 90 percent of said cross-sectional dimension of the platform.

19. The microsystem platform of claim 1, wherein the microsystem platform further comprises a multiplicity of air channels, exhaust air ports and air displacement channels.

20. The microsystem platform of claim 1, comprising a first layer and a second layer, wherein the first layer comprises sample reservoirs, reagent reservoirs and collection chambers, and the second layer comprises microchannels and mixing microchannels, wherein the sample reservoirs, reagent reservoirs and collection chambers in the first layer are fluidly connected by the microchannels and mixing microchannels in the second layer when the first layer is in contact with the second layer.

21. A centripetally-motivated fluid micromanipulation apparatus that is a combination of
   a microsystem platform according to claim 1, and
   a micromanipulation device, comprising a base, a rotating means, a power supply and user interface and operations controlling means, wherein the rotating means is operatively linked to the microsystem platform and in rotational contact therewith
   wherein a volume of a fluid within the microchannels of the platform is moved through said microchannels by centripetal force arising from rotational motion of the platform for a time and a rotational velocity sufficient to move the fluid through the microchannels.

22. The apparatus of claim 20, wherein the rotating means of the device is a motor.

23. The apparatus of claim 21, wherein the device comprises a rotational motion controlling means for controlling the rotational acceleration and velocity of the microsystem platform.

24. An apparatus of claim 21 wherein the micromanipulation apparatus further comprises an optical detector that measures absorbance, fluorescence, epifluorescence or chemoluminescence.

25. An apparatus of claim 21 wherein the micromanipulation apparatus further comprises a scanning, imaging, or confocal microscopy detector.

26. An apparatus of claim 21 wherein the micromanipulation apparatus further comprises a radiometric detector.

27. An apparatus of claim 21, 24, 25 or 26, wherein the detector is brought into alignment with the collection chamber on the platform by rotational motion of the microsystem platform.

28. The apparatus of claim 24, wherein the detector is an optical detector comprising a light source and a photodetector.

29. A method for homogenously mixing a sample and one or a plurality of reagents within the centripetally-motivated microsystem platform of claim 1, comprising the steps of:
   a) applying a volume of a fluid comprising a biological sample to one or a plurality of sample reservoirs of the microsystem platform when the platform is stationary, wherein the biological sample applied to each sample reservoir is the same or different;
   b) applying a volume of a solution comprising a reagent to one or a plurality of reagent reservoirs of the microsystem platform when the platform is stationary, wherein the biological sample applied to each sample reservoir is the same or different;
   c) rotating the platform at a rotational speed sufficient to motivate fluid flow from each sample reservoir and one or a plurality of reagent reservoirs into a mixing microchannel, wherein the platform is rotated for a time sufficient for the sample volume and reagent volume to traverse the mixing microchannel and be homogeneously mixed;
   d) delivering the mixture of the homogeneous mixture of the sample volume and reagent volume to a collection chamber; and e) collecting the homogenous mixture from the collection chamber.

30. A method according to claim 29, wherein the collection chamber further comprises a detection chamber, wherein the homogeneous mixture is detected in the detection chamber.

31. A method according to claim 29, wherein a component of the biological sample reacts with one or a plurality of reagents in the homogeneous mixture.

32. A method according to claim 30, wherein a component of the biological sample reacts with one or a plurality of reagents in the homogeneous mixture to form a reaction product, and the reaction product is detected.

33. A method according to claim 31, wherein the biological sample comprises an enzymatic species.

34. A method according to claim 32, wherein the biological sample comprises an enzymatic species.

35. A method for performing a biological or biochemical reaction within the centripetally-motivated microsystem platform of claim 1, comprising the steps of:

a) applying a volume of a fluid comprising a biological sample to one or a plurality of sample reservoirs of the microsystem platform when the platform is stationary, wherein the biological sample applied to each sample reservoir is the same or different and wherein the biological sample comprises one component of the biological or biochemical reaction;

b) applying a volume of a solution comprising a reagent to one or a plurality of reagent reservoirs of the microsystem platform when the platform is stationary, wherein the biological sample applied to each sample reservoir is the same or different and wherein one or a plurality of reagents comprises another component of the biological or biochemical reaction;

c) rotating the platform at a rotational speed sufficient to motivate fluid flow from each sample reservoir and one or a plurality of reagent reservoirs into a mixing microchannel, wherein the platform is rotated for a time sufficient for the sample volume and reagent volume to traverse the mixing microchannel and be homogeneously mixed;

d) delivering the mixture of the homogeneous mixture of the sample volume and reagent volume to a collection chamber;

e) collecting the homogenous mixture from the collection chamber; and f) detecting a product of the biological or biochemical reaction.

36. A method according to claim 35, wherein the collection chamber further comprises a detection chamber, wherein the product of the biological or biochemical reaction is detected in the detection chamber.

37. A method according to claim 35, wherein the biological sample comprises an enzymatic species.

38. A microsystem platform of claim 1 one of the plurality of reagent reservoirs is fluidly connected to a metering manifold comprising a multiplicity of metering capillaries, wherein a metered amount of reagent solution is delivered to each of a multiplicity of mixing microchannels from one of the multiplicity of metering capillaries.

39. A microsystem platform of claim 1 wherein the microchannel connecting a sample reservoir to a mixing microchannel has a larger interior dimension than one or a plurality of microchannels fluidly connecting one or a plurality of reagent reservoirs to the mixing microchannel, wherein fluid flow through the microchannel from the sample reservoir promotes fluid flow from the reagent reservoir into the mixing microchannel.

40. A microsystem platform of claim 1 wherein the microchannel connecting a sample reservoir to a mixing microchannel has a smaller interior dimension than one or a plurality of microchannels fluidly connecting one or a plurality of reagent reservoirs to the mixing microchannel, wherein fluid flow through the microchannel from the reagent reservoir promotes fluid flow from the sample reservoir into the mixing microchannel.

* * * * *